(12) United States Patent
Soreefan et al.

(10) Patent No.: US 12,138,044 B2
(45) Date of Patent: Nov. 12, 2024

(54) SYSTEMS AND METHODS FOR DETERMINING SUBJECT POSITIONING AND VITAL SIGNS

(71) Applicant: HILL-ROM SERVICES, INC., Batesville, IN (US)

(72) Inventors: Ibne Soreefan, West Chester, OH (US); Eric Agdeppa, Cincinnati, OH (US); Yongji Fu, Harrison, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 18/451,377

(22) Filed: Aug. 17, 2023

(65) Prior Publication Data
US 2023/0389826 A1 Dec. 7, 2023

Related U.S. Application Data

(63) Continuation of application No. 16/679,442, filed on Nov. 11, 2019, now abandoned.
(Continued)

(51) Int. Cl.
*A61B 5/00* (2006.01)
*A61B 5/0205* (2006.01)
(Continued)

(52) U.S. Cl.
CPC .......... *A61B 5/1128* (2013.01); *A61B 5/0008* (2013.01); *A61B 5/0013* (2013.01);
(Continued)

(58) Field of Classification Search
CPC ... A61B 5/1128; A61B 5/0008; A61B 5/0013; A61B 5/0205; A61B 5/1135;
(Continued)

(56) References Cited

U.S. PATENT DOCUMENTS

| 7,035,432 B2 | 4/2006 | Szuba |
| 8,849,379 B2 | 9/2014 | Abreu |

(Continued)

FOREIGN PATENT DOCUMENTS

| EP | 2227794 A1 | 9/2010 |
| EP | 2619724 A2 | 7/2013 |

(Continued)

OTHER PUBLICATIONS

Extended European Search Report for European Application No. 19208732.8 dated Apr. 3, 2020, 8 pages.
(Continued)

*Primary Examiner* — Joel Lamprecht
*Assistant Examiner* — Gabriel Victor Popescu
(74) *Attorney, Agent, or Firm* — Dinsmore & Shohl LLP

(57) ABSTRACT

Systems and methods for monitoring a positioning and vital signs of a subject are disclosed. A method includes receiving, by a processing device of a monitoring device, LWIR image data from a first imaging component of the monitoring device and NIR image data from a second imaging component of the monitoring device, determining one or more boundaries of the patient support apparatus from the NIR image data, constructing one or more virtual boundaries that correspond to the boundaries of the patient support apparatus, determining a location of the subject with respect to the virtual boundaries from at least one of the LWIR image data and the NIR image data, determining a facial temperature and a heart rate of the subject from the LWIR image data, and determining a respiration rate of the subject from at least one of the LWIR image data and the NIR image data.

10 Claims, 14 Drawing Sheets

Related U.S. Application Data

(60) Provisional application No. 62/768,334, filed on Nov. 16, 2018.

(51) Int. Cl.
*A61B 5/11* (2006.01)
*A61B 5/113* (2006.01)
*G06T 7/00* (2017.01)

(52) U.S. Cl.
CPC .......... *A61B 5/0205* (2013.01); *A61B 5/1135* (2013.01); *G06T 7/0012* (2013.01); *G06T 2207/10048* (2013.01); *G06T 2207/30201* (2013.01)

(58) Field of Classification Search
CPC ......... G06T 7/0012; G06T 2207/10048; G06T 2207/30201; G01J 5/10; G01K 7/00; G08B 21/043; H04N 5/33; H04N 7/18; H04N 21/4348
See application file for complete search history.

(56) References Cited

U.S. PATENT DOCUMENTS

| | | | |
|---|---|---|---|
| 9,843,743 B2 | 12/2017 | Lewis et al. | |
| 9,901,306 B2* | 2/2018 | Adams | A61B 5/725 |
| 2007/0225614 A1 | 9/2007 | Naghavi et al. | |
| 2008/0159591 A1 | 7/2008 | Ruedin | |
| 2012/0289850 A1 | 11/2012 | Xu et al. | |
| 2013/0240735 A1* | 9/2013 | Yen | G06T 2207/100 250/340 |
| 2014/0183362 A1* | 7/2014 | Islam | A61B 5/0022 250/338.4 |
| 2014/0253709 A1 | 9/2014 | Bresch et al. | |
| 2014/0275832 A1 | 9/2014 | Muehlsteff et al. | |
| 2015/0190061 A1 | 7/2015 | Godavarty et al. | |
| 2016/0015277 A1 | 1/2016 | Dumoulin et al. | |
| 2016/0120482 A1* | 5/2016 | Kirenko | A61B 5/0077 |
| 2016/0206216 A1* | 7/2016 | Kirenko | A61B 5/0077 |
| 2016/0310791 A1 | 10/2016 | Fauci | |
| 2017/0302864 A1 | 10/2017 | Southerland et al. | |
| 2018/0121762 A1 | 5/2018 | Han | |
| 2018/0186234 A1 | 7/2018 | Mestha et al. | |
| 2019/0008387 A1* | 1/2019 | Godavarty | A61B 5/7435 |
| 2019/0266872 A1* | 8/2019 | Nitta | A61B 5/0022 |
| 2019/0350471 A1* | 11/2019 | Marks | A61B 5/7203 |

FOREIGN PATENT DOCUMENTS

| | | |
|---|---|---|
| JP | 2009183560 A | 8/2009 |
| JP | 2017168105 A | 9/2017 |
| KR | 101715218 B1 | 3/2017 |
| WO | 2015018675 A1 | 2/2015 |
| WO | 2015062969 A1 | 5/2015 |
| WO | 2018047795 A1 | 3/2018 |

OTHER PUBLICATIONS

Amelard, R. et al. "Non-contact hemodynamic imaging reveals the jugular venous pulse waveform." Scientific Reports, vol. 7, Article No. 40150, Jan. 9, 2017. DOI: 10.1038/srep40150.

Bagavathiappan, S et al. "Infrared thermal imaging for detection of peripheral vascular disorders." Journal of medical physics vol. 34, 1 (2009): 43-7. doi: 10.4103/0971-6203.48720.

Pereira, Carina Barbosa et al. "Remote monitoring of breathing dynamics using infrared thermography." Biomedical optics express vlol. 6, 11 4378-94. Oct. 16, 2015, doui:10.1364/BOE.6.004378.

* cited by examiner

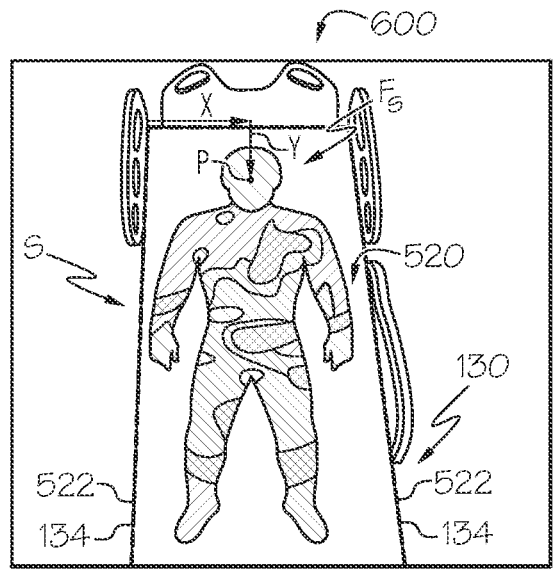 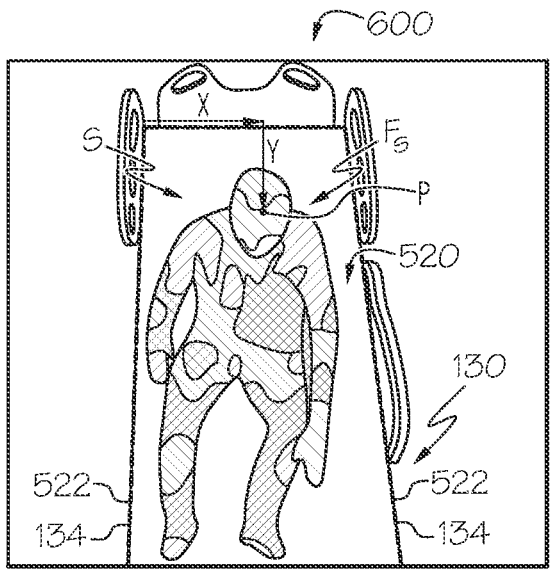
FIG. 6A  FIG. 6B
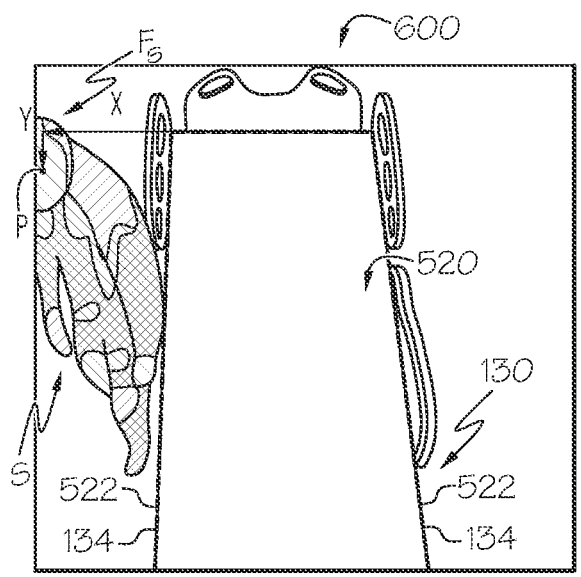 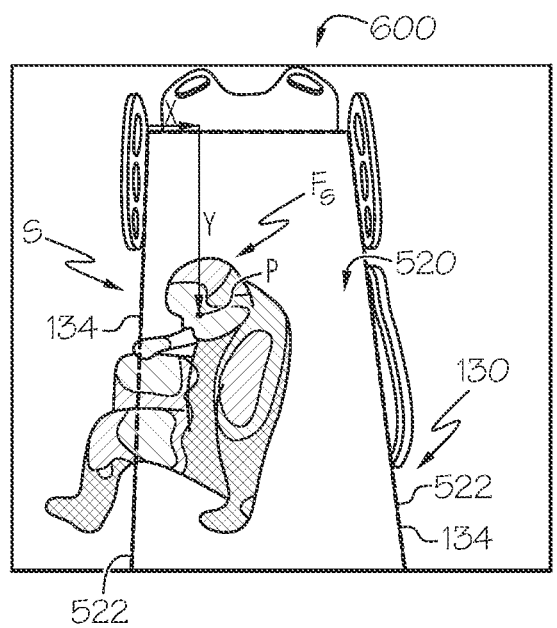
FIG. 6C  FIG. 6D

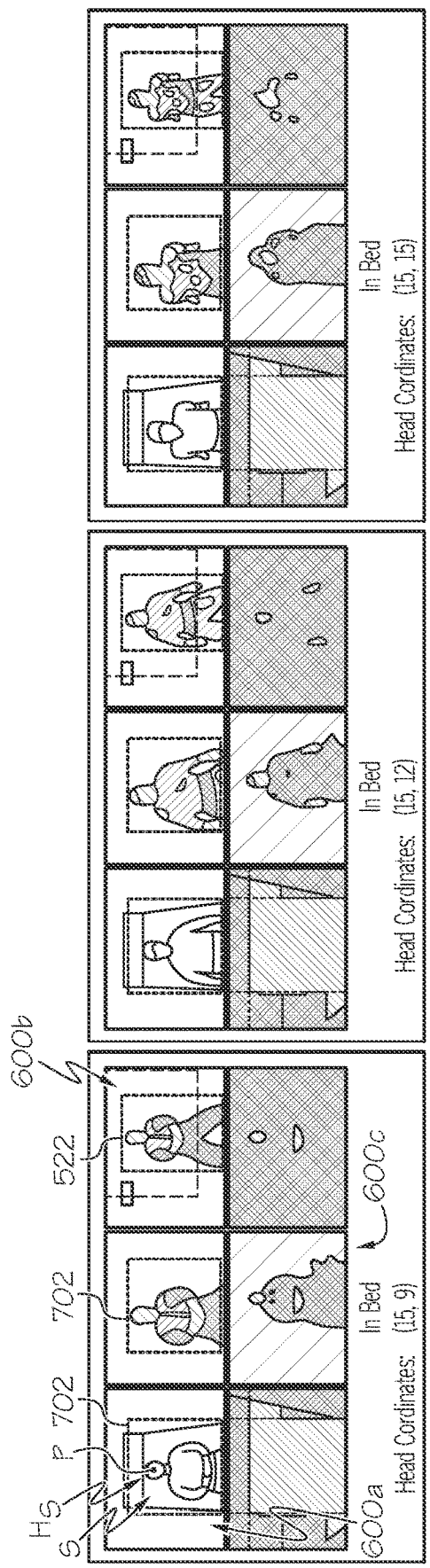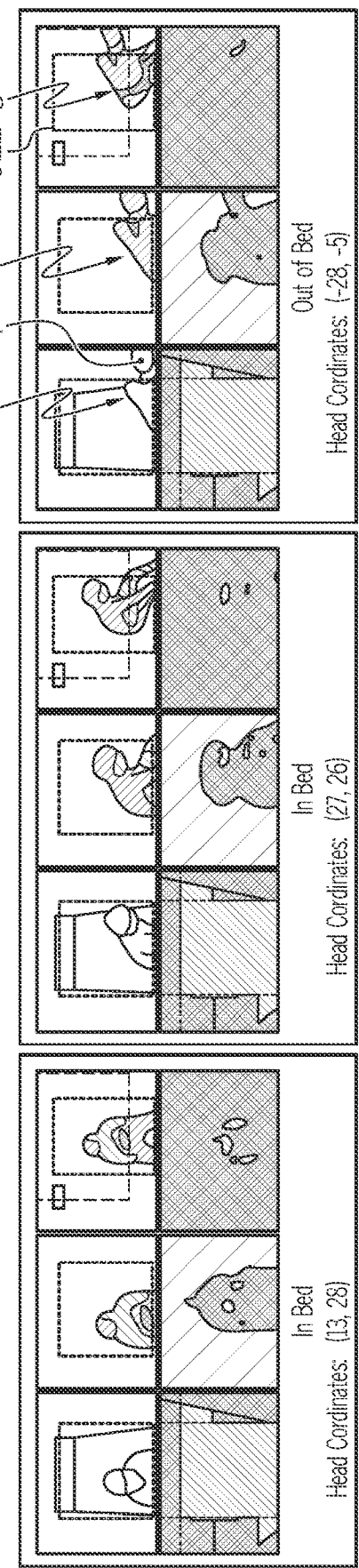

SYSTEMS AND METHODS FOR DETERMINING SUBJECT POSITIONING AND VITAL SIGNS

CROSS-REFERENCE TO RELATED APPLICATION

This application is a continuation of U.S. patent application Ser. No. 16/679,442, filed on Nov. 11, 2019, which claims the benefit of U.S. Provisional Application Ser. No. 62/768,334, filed on Nov. 16, 2018, entitled "Systems and Methods for Determining Subject Positioning and Vital Signs," the contents of which is incorporated by reference herein in its entirety.

BACKGROUND

Field

The present specification generally relates to subject tracking and monitoring systems and methods and, more specifically, to tracking and monitoring systems and methods that utilize a plurality of imaging devices to monitor subject positioning, movement, and vital signs.

Technical Background

It may be necessary to determine and/or track a subject's positioning when the subject is in a patient support apparatus, such as a hospital bed. For example, subjects may be under orders to remain in the patient support apparatus, but may not do so. In addition, it may be necessary to monitor the subject's facial temperature, heart rate, and respiration rate concurrently with the subject's positioning. Existing methods do not allow for such a concurrent monitoring with the same device. As such, multiple devices that do not communicate with one another are necessary, which takes up an excessive amount of space and requires extra human involvement to monitor the multiple devices.

Accordingly, a need exists for systems and methods that provide medical personnel with an ability to monitor a subject's positioning, facial temperature, heart rate, and respiration rate concurrently.

SUMMARY

In one aspect, a method of automatically monitoring a position and vital signs of a subject supported by a patient support apparatus includes receiving, by a processing device of a monitoring device, long wave infrared (LWIR) image data from a first imaging component of the monitoring device and near infrared (NIR) image data from a second imaging component of the monitoring device. The method further includes determining, by the processing device, one or more boundaries of the patient support apparatus from the NIR image data, constructing, by the processing device, one or more virtual boundaries that correspond to the one or more boundaries of the patient support apparatus, determining, by the processing device, a location of the subject with respect to the one or more virtual boundaries from at least one of the LWIR image data and the NIR image data, determining, by the processing device, a facial temperature and a heart rate of the subject from the LWIR image data, and determining, by the processing device, a respiration rate of the subject from at least one of the LWIR image data and the NIR image data. In another aspect, the method further includes transmitting, by the processing device, at least one of the following to a user device: the LWIR image data, the NIR image data, data corresponding to the one or more virtual boundaries, data corresponding to the location of the subject, data corresponding to the facial temperature of the subject, data corresponding to the heart rate of the subject, and data corresponding to the respiration rate of the subject. In another aspect, the method further includes directing, by the processing device, one or more light emitting components to emit NIR light towards the subject. In another aspect, determining the heart rate of the subject includes determining, from the NIR image data, an amount of the NIR light emitted by the one or more light emitting components that is absorbed by oxygenated blood present in capillaries of a face of the subject over a period of time. The amount of NIR light that is absorbed cycles between a maximum amount absorbed and a minimum amount absorbed, and wherein a heartbeat corresponds to each cycle. In another aspect, determining the one or more boundaries of the patient support apparatus from the NIR image data includes utilizing an object recognition algorithm to determine the patient support apparatus from the NIR image data based on a shape and a size of the patient support apparatus and determine one or more edges of the patient support apparatus. In another aspect, determining the location of the subject with respect to the one or more virtual boundaries includes utilizing one or more of a facial recognition algorithm and an object recognition algorithm to determine a subject head position from at least one of the LWIR image data and the NIR image data, establishing a point that corresponds to the subject head position, and tracking movement of the point as the subject head position changes. In another aspect, determining the respiration rate of the subject includes utilizing an object detection algorithm to identify a subject chest cavity from the at least one of the LWIR image data and the NIR image data, and monitoring a chest expansion and contraction movement over a period of time.

In another aspect, a monitoring device for monitoring a position and vital signs of a subject supported by a patient support apparatus includes a first imaging component that obtains long wave infrared (LWIR) image data of the subject, a second imaging component that obtains near infrared (NIR) image data of the subject and the patient support apparatus, a processing device, and a non-transitory, processor-readable storage medium including one or more programming instructions thereon. The one or more programming instructions, when executed, cause the processing device to receive LWIR image data from the first imaging component and NIR image data from the second imaging component, determine one or more boundaries of the patient support apparatus from the NIR image data, construct one or more virtual boundaries that correspond to the one or more boundaries of the patient support apparatus, determine a location of the subject with respect to the one or more virtual boundaries from at least one of the LWIR image data and the NIR image data, determine a facial temperature and a heart rate of the subject from the LWIR image data, and determine a respiration rate of the subject from at least one of the LWIR image data and the NIR image data. In another aspect the monitoring device further includes network interface hardware that communicatively couples the monitoring device to a network. In another aspect, the non-transitory, processor-readable storage medium further includes one or more programming instructions that, when executed, cause the processing device to transmit at least one of the following via the network interface hardware to a user device: the LWIR image data, the NIR image data, data corresponding to the one or more virtual boundaries, data corresponding to the location of the subject, data corresponding to the facial temperature of the subject, data corresponding to the heart rate of the subject, and data corresponding to the respiration rate of the subject. In another aspect, the monitoring device further includes one or more light emitting components that emit NIR light. In another aspect, the non-transitory, processor-readable storage medium further includes one or more programming instructions that, when executed, cause the processing device to direct the one or more light emitting components to emit the NIR light towards the subject. In another aspect, the one or more programming instructions that, when executed, cause the processing device to determine the heart rate of the subject further cause the processing device to determine, from the NIR image data, an amount of the NIR light emitted by the one or more light emitting components that is absorbed by oxygenated blood present in capillaries of a face of the subject over a period of time, wherein the amount of NIR light that is absorbed cycles between a maximum amount absorbed and a minimum amount absorbed, and wherein a heartbeat corresponds to each cycle. In another aspect, the first imaging component includes a first optical axis, the second imaging component includes a second optical axis, the first imaging component is oriented such that the first optical axis forms a first angle relative to a surface of the patient support apparatus, the second imaging component is oriented such that the second optical axis forms a second angle relative to the surface of the patient support apparatus, and the first angle is different from the second angle.

In yet another aspect, a system for monitoring a position and vital signs of a subject supported by a patient support apparatus includes a monitoring device. The monitoring device includes a first imaging component that obtains long wave infrared (LWIR) image data of the subject and a second imaging component that obtains near infrared (NIR) images of the subject and the patient support apparatus. The monitoring device is programmed to receive LWIR image data from the first imaging component and NIR image data from the second imaging component, determine one or more boundaries of the patient support apparatus from the NIR image data, construct one or more virtual boundaries that correspond to the one or more boundaries of the patient support apparatus, determine a location of the subject with respect to the one or more virtual boundaries from at least one of the LWIR image data and the NIR image data, determine a facial temperature and a heart rate of the subject from the LWIR image data, and determine a respiration rate of the subject from at least one of the LWIR image data and the NIR image data. In another aspect, the system further includes a user device communicatively coupled to the monitoring device. The user device includes a display that displays at least one of the LWIR image data, the NIR image data, the one or more virtual boundaries, the location of the subject with respect to the one or more virtual boundaries, the facial temperature of the subject, the respiration rate of the subject, and the heart rate of the subject. In another aspect, the user device is remotely located from the monitoring device. In another aspect, the monitoring device further includes one or more light emitting components that emit NIR light. In another aspect, the monitoring device is further programmed to direct the one or more light emitting components to emit the NIR light towards the subject. In another aspect, the monitoring device is further programmed to determine, from the NIR image data, an amount of the NIR light emitted by the one or more light emitting components that is absorbed by oxygenated blood present in capillaries of a face of the subject over a period of time, wherein the amount of NIR light that is absorbed cycles between a maximum amount absorbed and a minimum amount absorbed, and wherein a heartbeat corresponds to each cycle. In another aspect, the first imaging component includes a first optical axis, the second imaging component includes a second optical axis, the first imaging component is oriented such that the first optical axis forms a first angle relative to a surface of the patient support apparatus, the second imaging component is oriented such that the second optical axis forms a second angle relative to the surface of the patient support apparatus, and the first angle is different from the second angle. In another aspect, the monitoring device is coupled to a ceiling of a space.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 6A schematically depicts an illustrative screen shot of an image obtained by a monitoring device showing a subject in a supine position according to one or more embodiments shown or described herein;

FIG. 6B schematically depicts an illustrative screen shot of an image obtained by a monitoring device showing a subject in a sitting position within patient support apparatus boundaries according to one or more embodiments shown or described herein;

FIG. 6C schematically depicts an illustrative screen shot of an image obtained by a monitoring device showing a subject in a standing position outside patient support apparatus boundaries according to one or more embodiments shown or described herein;

FIG. 6D schematically depicts an illustrative screen shot of an image obtained by a monitoring device showing a subject in a sitting position partially outside patient support apparatus boundaries according to one or more embodiments shown or described herein;

FIG. 7A schematically depicts an illustrative user interface for monitoring subject positioning that shows a subject laying in a patient support apparatus according to one or more embodiments shown or described herein;

FIG. 7B schematically depicts an illustrative user interface for monitoring subject positioning that shows a subject laying in a patient support apparatus according to one or more embodiments shown or described herein;

FIG. 7C schematically depicts an illustrative user interface for monitoring subject positioning that shows a subject sitting up in a patient support apparatus according to one or more embodiments shown or described herein;

FIG. 7D schematically depicts an illustrative user interface for monitoring subject positioning that shows a subject sitting up in a patient support apparatus according to one or more embodiments shown or described herein;

FIG. 7E schematically depicts an illustrative user interface for monitoring subject positioning that shows a subject sitting on an edge of a patient support apparatus according to one or more embodiments shown or described herein;

FIG. 7F schematically depicts an illustrative user interface for monitoring subject positioning that shows a subject out of a patient support apparatus according to one or more embodiments shown or described herein;

DETAILED DESCRIPTION

Figure 1:
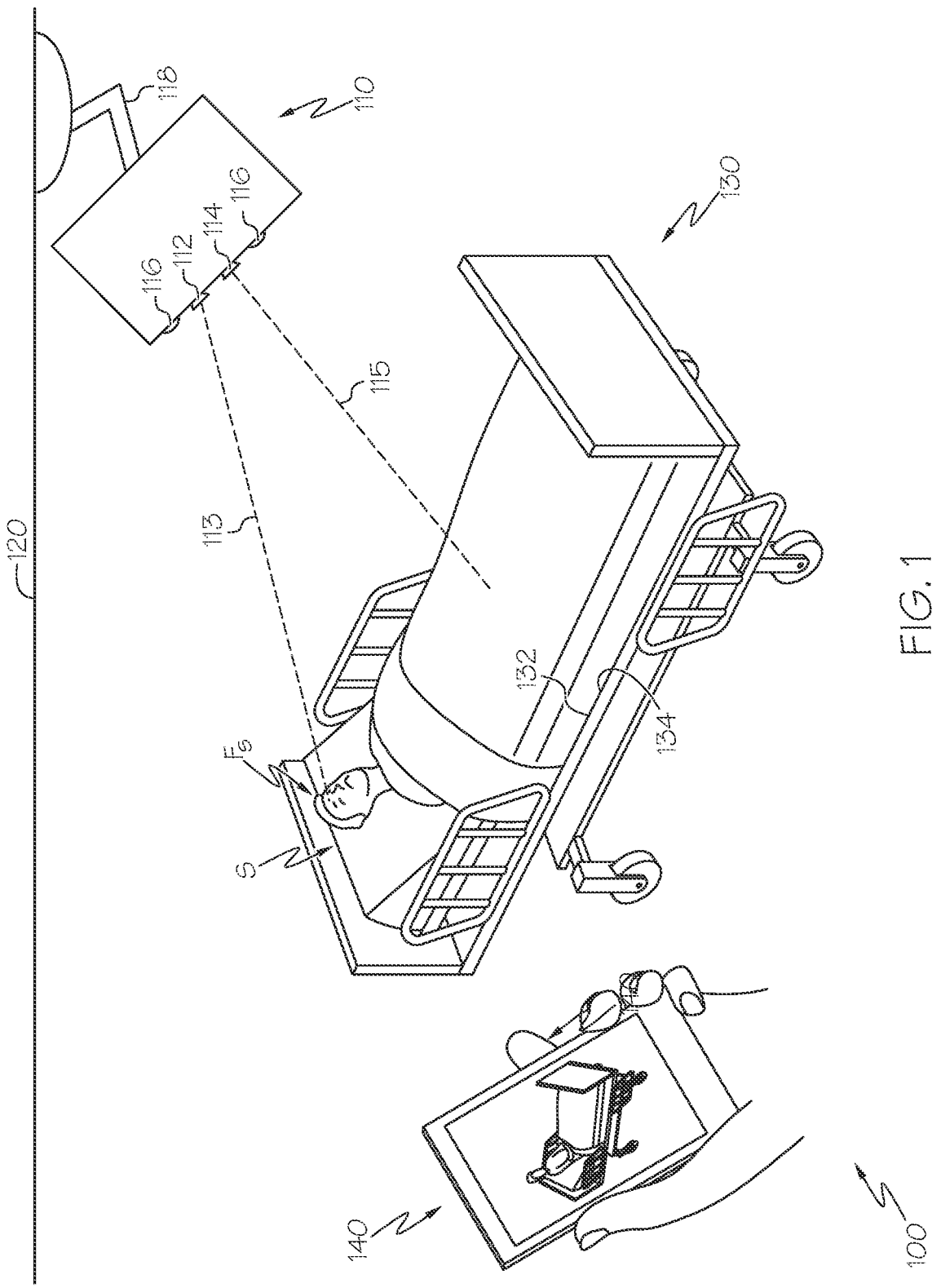
FIG. 1 schematically depicts an illustrative subject monitoring system according to one or more embodiments shown or described herein.

Reference will now be made in detail to embodiments of systems and methods for concurrently determining a positioning, a temperature, a heart rate, and a respiration rate of a subject, examples of which are illustrated in the accompanying drawings. Whenever possible, the same reference numerals will be used throughout the drawings to refer to the same or like parts. One embodiment of a system for concurrently determining a positioning, a temperature, a heart rate, and a respiration rate of a subject is depicted in FIG. 1, in which the system includes a monitoring device having a plurality of imaging devices and one or more light emitting diodes, and a user device communicatively coupled to the monitoring device. The monitoring device is generally positioned such that it faces a subject and obtains images of the subject from the plurality of imaging devices. The monitoring device and/or the user device concurrently determines a positioning, a facial temperature, a heart rate, and a respiration rate of the subject from the images. Information relating to the positioning, facial temperature, heart rate, and respiration rate is provided via a user interface to a user. Accordingly, the positioning, temperature, heart rate, and respiration rate of a subject can be accurately tracked such that, if the subject moves and/or if the subject's temperature, heart rate, and/or respiration fluctuates beyond a threshold, a user can be alerted to the movement and/or fluctuation. In addition, the positioning of the monitoring device allows for non-invasive and non-contact monitoring of the subject, which may be necessary for monitoring subjects in sterile fields. Additionally, the location of the monitoring device allows for constant monitoring of a subject in a high traffic area without a concern of bumping or otherwise moving the positioning of the monitoring devices with respect to the objects being monitored, thereby ensuring constant accurate monitoring. Further, the subject does not need to be physically connected to monitoring devices that may hinder subject movement, be uncomfortable, fall off, and/or the like.

As used herein, the term "vital signs" generally refers to a collective temperature, heart rate, and respiration rate of a subject. It should be understood that other vital signs may also be included and monitored herein in addition to the collective monitoring of a temperature, a heart rate, and a respiration rate of a subject.

The phrase "communicatively coupled" is used herein to describe the interconnectivity of various components of the system for monitoring the positioning and the vital signs of a subject and means that the components are connected either through wires, optical fibers, or wirelessly such that electrical, optical, and/or electromagnetic signals may be exchanged between the components. It should be understood that other means of connecting the various components of the system not specifically described herein are included without departing from the scope of the present disclosure.

As used herein, the term "positioning" generally refers to how a subject is oriented on a surface, such as a patient support apparatus or the like. Positioning, as used herein, may generally relate to a positioning of a subject with respect to the surface based on measurements taken from image data relating to the subject's face. However, it should be understood that positioning may be determined from other characteristics of a subject's body. Illustrative examples of a subject's positioning relative to a surface may include a supine positioning (e.g., the subject is laying on a patient support apparatus), a sitting position (e.g., the subject is sitting up in the patient support apparatus or sitting on the edge of the patient support apparatus), a standing position, and/or the like.

Referring to FIG. 1, a system 100 for concurrently determining a positioning, a temperature, a heart rate, and a respiration rate of a subject is depicted. The system 100 includes a monitoring device 110 communicatively coupled to a user device 140. The monitoring device 110 includes a first imaging component 112, a second imaging component 114, and one or more light emitting components 116. While FIG. 1 depicts two light emitting components 116, it should be understood that any number of light emitting components 116 may be used.

Also depicted in FIG. 1 is a patient support apparatus 130 supporting a subject S on a surface 132 thereof. The surface 132 is generally any supportive component for supporting the subject S, particularly when the subject S is receiving medical care. The surface 132 of the patient support apparatus 130 is defined by one or more boundaries 134. The one or more boundaries 134 are generally the edges of the patient support apparatus 130. In some nonlimiting examples, the patient support apparatus 130 may be an operating table, a gurney, a hospital bed, and/or a person support apparatus.

The monitoring device 110 is generally positioned with respect to the patient support apparatus 130 such that the first imaging component 112, the second imaging component 114, and the light emitting components 116 are aimed at the patient support apparatus 130. That is, a first optical axis 113 of the first imaging component 112 and a second optical axis 115 of the second imaging component 114 each extends towards at least a portion of the subject S (e.g., the subject's face $F_S$), the surface 132 of the patient support apparatus 130, and/or the other objects. In the embodiments described herein, the optical axes 113, 115 refer to an imaginary line defining the path along which electromagnetic radiation propagates to and through each respective imaging component 112, 114. The respective angles of the optical axes 113, 115 may be different from one another. Accordingly, a field of view of the first imaging component 112 includes at least a portion of the patient support apparatus 130 and a field of view of the second imaging component 114 includes at least a portion of the patient support apparatus 130, but not necessarily the same portions of the patient support apparatus 130. In addition, the positioning of the monitoring device 110 is such that the light emitting components 116 emit light that is generally aimed toward the patient support apparatus 130 and/or a portion thereof, particularly the subject's face $F_S$.

FIG. 1 depicts the monitoring device 110 as being mounted on a ceiling 120 of a space containing the patient support apparatus 130. That is, the monitoring device 110 is coupled to the ceiling 120 via a mounting arm 118 or the like. In some embodiments, the monitoring device 110 may be in a fixed position on the ceiling 120 such that the monitoring device 110 is not movable. In other embodiments, the monitoring device 110 may be movable with respect to the ceiling 120. For example, the mounting arm 118 may be an articulating arm that extends or retracts to move the monitoring device 110 relative to the ceiling 120. In another example, the mounting arm 118 may be coupled to a carriage that is movable along one or more tracks mounted on the ceiling 120. In yet another example, the monitoring device 110 may be rotatably mounted to an end of the mounting arm 118 such that the monitoring device 110 can be movable relative to the mounting arm 118 (e.g., in a ball and socket configuration).

While the monitoring device 110 is shown as being mounted to the ceiling 120 of the space in FIG. 1, it should be understood that this is merely illustrative. In other embodiments, the monitoring device 110 may be mounted to a wall, mounted in a corner, mounted to the patient support apparatus 130, suspended from beams or other devices, coupled to stands, coupled to surgical lights, and/or the like. The monitoring device 110 may generally be mounted such that the first imaging component 112, the second imaging component 114, and the one or more light emitting components maintain their positioning relative to the patient support apparatus (e.g., such that the optical axes 113, 115 remain particularly aimed) without a risk of being bumped or otherwise moved by individuals, other equipment, and/or the like, particularly in high-traffic areas (such as an operating room, a recovery room, or the like). In addition, the mounting position may be such so that the entire patient support apparatus 130 and the subject S therein can be imaged by at least one of the first imaging component 112 and the second imaging component 114.

The first imaging component 112 of the monitoring device 110 is generally a thermal camera, particularly a long wave infrared (LWIR) thermal camera. That is, the first imaging component 112 may be any imaging device that is suitable for obtaining images within the LWIR spectrum. As used herein, the terms "images" or "image" that are obtained by the first imaging component 112 refer to video images (i.e., a sequence of consecutive images) and/or still images (including still images isolated from video images) captured in at least the LWIR spectrum. That is, the first imaging component 112 may be a device that obtains images via IR thermography to capture radiation in the long-infrared range of the electromagnetic spectrum. The long-infrared range of the electromagnetic spectrum may be electromagnetic radiation having a wavelength from about 8 micrometers (µm) to about 14 µm, including about 8 µm, about 9 µm, about 10 µm, about 11 µm, about 12 µm, about 13 µm, about 14 µm or any value or range between any two of these values (including endpoints). A nonlimiting example of the first imaging component 112 may be the FUR® Lepton® LWIR micro thermal camera module sold by FLIR Systems, Inc. (Wilsonville, OR).

Since IR radiation is emitted by all objects having a temperature above absolute zero, the first imaging component 112, in obtaining images via IR thermography, can image an environment with or without visible illumination. The first imaging component 112 obtains images based on temperature and the resulting images indicate variations in temperature. Thus, in the images produced by the first imaging component 112, objects are distinguishable from one another and the background based on variations in temperature. For example, humans become distinguishable in a typical room temperature environment because their body temperatures are greater than objects that are at or below room temperature and because the human body emits IR radiation at a different temperature than such objects at, below, or above room temperature. Illustrative examples of images that solely depict temperature variations are shown and described herein with respect to FIGS. 7A-7F.

Still referring to FIG. 1, the first imaging component 112 can image certain target objects (such as the subject S, the surface 132 of the patient support apparatus 130, and/or other objects) even if the field of view between the first imaging component 112 and the target object is obstructed or partially obstructed by items that are at a lower temperature and allow thermal energy to penetrate therethrough. This is because the target object radiates thermal energy that extends around and/or through the obstruction. For example, if the field of view for a first imaging component 112 is partially blocked by an obstruction such as a sheet, a surgical drape, a hospital gown, clothing, and/or the like, the first imaging component 112 may nevertheless detect the IR radiation emitted by the target object if the target object emits sufficient thermal energy to pass around and/or through the obstruction.

The second imaging component 114 of the monitoring device 110 may be a thermal camera and/or a camera that obtains thermal images and images in the visible spectrum. In embodiments where the second imaging component 114 is a thermal camera, the second imaging component 114 may be a near infrared (NIR) camera. That is, the second imaging component 114 may be any imaging device that is suitable for obtaining images at least within the NIR spectrum. In embodiments where the second imaging component 114 further obtains images in the visible spectrum, the second imaging component 114 may be an RGB camera. That is, the second imaging component 114 may be any imaging device that is suitable for obtaining images at least within the NIR spectrum, but may optionally include obtaining images in the visible spectrum. Nonlimiting examples of such cameras include a multispectral camera and an enhanced RGB camera.

As used herein, the terms "images" or "image" that are obtained by the second imaging component 114 refer to video images (i.e., a sequence of consecutive images) and/or still images (including still images isolated from video images) captured in the NIR spectrum and/or the visible spectrum. That is, the second imaging component 114 may be a device that obtains images via IR thermography to capture radiation in the near-infrared range of the electromagnetic spectrum and/or may be a device that obtains images via RGB imaging to capture radiation in the visible range of the electromagnetic spectrum. The near-infrared range of the electromagnetic spectrum may be electromagnetic radiation having a wavelength from about 0.75 micrometers (μm) to about 1.7 μm, including about 0.75 μm, about 0.8 μm, about 0.9 μm, about 1.0 μm, about 1.1 μm, about 1.2 μm, about 1.3 μm, about 1.4 μm, about 1.5 μm, about 1.6 μm, about 1.7 μm, or any value or range between any two of these values (including endpoints). Nonlimiting examples of the second imaging component 114 may include the FLIR® Boson™ SWIR camera core sold by FLIR Systems, Inc. (Wilsonville, OR), the FluxData FD-3SWIR camera sold by FluxData, Inc. (Rochester, NY), and the Spectral Devices Multispectral camera sold by Spectral Devices Inc. (London, ON).

Each of the one or more light emitting components 116 is generally a light emitting diode (LED) that emits a particular wavelength of light. For example, each of the one or more light emitting components 116 may be particularly configured to emit light in the near-infrared spectrum. That is, each of the one or more light emitting components 116 may be a solid state p-n junction device that emit light when forward biased, the light having a wavelength from about 0.75 micrometers (μm) to about 1.7 μm, including about 0.75 μm, about 0.8 μm, about 0.9 μm, about 1.0 μm, about 1.1 μm, about 1.2 μm, about 1.3 μm, about 1.4 μm, about 1.5 μm, about 1.6 μm, about 1.7 μm, or any value or range between any two of these values (including endpoints). In some embodiments, each of the one or more light emitting components 116 may be arranged such that the light emitted therefrom is aimed in a particular direction toward a target, such as toward the subject S, the subject's face $F_S$, the surface 132 of the patient support apparatus 130, or the like. In some embodiments, a plurality of light emitting components 116 may be arranged to emit a particular pattern of light toward the target.

The first imaging component 112 and the second imaging component 114 may be spaced apart or may be arranged next to each other within the monitoring device 110. For example, each of the first imaging component 112 and the second imaging component 114 may be spaced at a distance from each other such that the respective optical axes 113, 115 of each of the first imaging component 112 and the second imaging component 114 is at a different angle with respect to the surface 132 of the patient support apparatus 130. For example, in embodiments, the first imaging component 112 and the second imaging component 114 may be oriented relative to one another and the surface 132 of the patient support apparatus 130 such that the optical axes 113, 115 thereof are non-parallel with one another, as depicted in FIG. 1. As such, the first imaging component 112 and the second imaging component 114 each capture a different angle of the subject S, the subject's face $F_S$, the surface 132 of the patient support apparatus 130, and/or other objects. The distance between the first imaging component 112 and the second imaging component 114 is not limited by this disclosure, and may generally be any distance. In another example, the first imaging component 112 and the second imaging component 114 may be arranged next to each other and the first imaging component 112 is configured to obtain an image that partially overlaps an image obtained by the second imaging component 114 such that the images therefrom can be compared when conducting an analysis of the positioning of the subject S, the location of the subject's face $F_S$, a facial temperature of the subject S, a heart rate of the subject S, and/or a respiration rate of the subject S.

Figure 2:
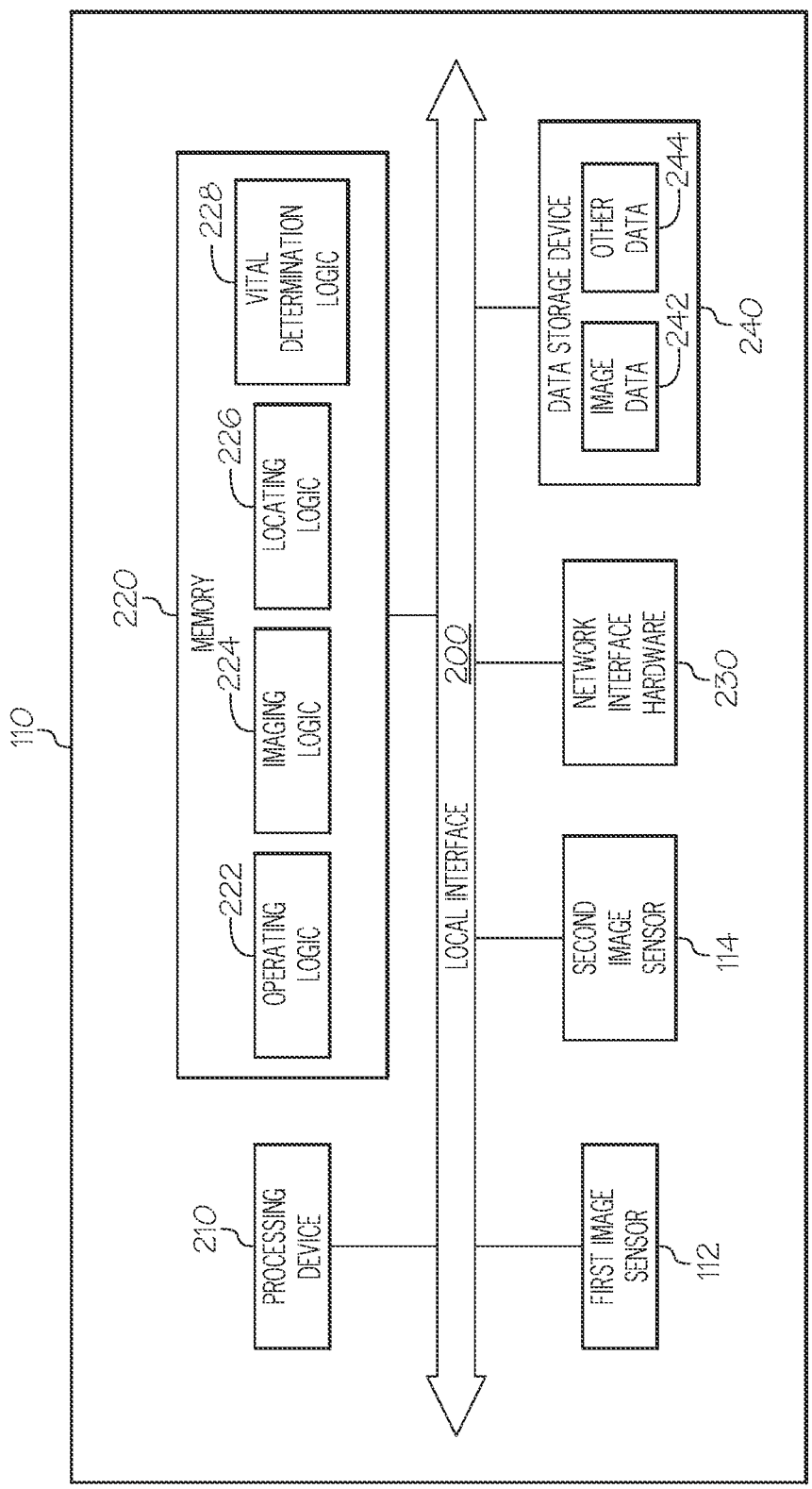
FIG. 2 schematically depicts a block diagram of illustrative internal components of a monitoring device within a subject monitoring system according to one or more embodiments shown or described herein.

In addition to the first imaging component 112, the second imaging component 114, and the one or more light emitting components 116, the monitoring device 110 may also include one or more internal components that provide functionality of the monitoring device 110. FIG. 2 depicts illustrative internal components within the monitoring device 110 in some embodiments. As depicted in FIG. 2, the monitoring device 110 may further include a local interface 200 (e.g., a bus) that communicatively interconnects the various components, including, but not limited to, a processing device 210, memory 220, network interface hardware 230, a data storage device 240, the first imaging component 112, and/or the second imaging component 114.

The processing device 210, such as a computer processing unit (CPU), may be the central processing unit of the monitoring device 110, performing calculations and logic operations required to execute a program. The processing device 210, alone or in conjunction with one or more of the other elements disclosed in FIG. 2, is an illustrative processing device, computing device, processor, or combination thereof, as such terms are used in this disclosure.

The memory 220, such as read only memory (ROM) and random access memory (RAM), may constitute illustrative memory devices (i.e., non-transitory, processor-readable storage media). Such memory 220 may include one or more programming instructions thereon that, when executed by the processing device 210, cause the processing device 210 to complete various processes, such as the processes described herein. Optionally, the program instructions may be stored on a tangible computer-readable medium such as a digital disk, flash memory, a memory card, a USB drive, an optical disc storage medium (e.g., Blu-ray™, CD, DVD), and/or other non-transitory processor-readable storage media.

In some embodiments, the program instructions contained on the memory 220 may be embodied as a plurality of software modules, where each module provides programming instructions for completing one or more tasks. For example, as shown in FIG. 2, the memory 220 may contain one or more of operating logic 222, imaging logic 224, locating logic 226, and vital determination logic 228. The operating logic 222 may include an operating system and/or other software for managing components of the monitoring device 110. The imaging logic 224 may generally include programming instructions for directing operation of the first imaging component 112 and/or the second imaging component 114 for the purposes of obtaining images from the first imaging component 112 and/or the second imaging component 114. For example, the imaging logic 224 may direct the first imaging component 112 and/or the second imaging component 114 to turn on/off, to collect images, to adjust settings, and/or the like. The locating logic 226 may generally include programming instructions for determining a location of the subject S on the surface 132 of the patient support apparatus 130 based on images received from the first imaging component 112 and/or the second imaging component 114. Referring to FIGS. 1 and 2, the vital determination logic 228 may generally include programming instructions for determining vital signs of the subject S, including a body temperature (e.g., a facial temperature), a heart rate, and/or a respiration rate of the subject S, based on the images received from the first imaging component 112 and/or the second imaging component 114. It should be understood that the various logic modules described herein with respect to FIG. 2 are merely illustrative, and that other logic modules, including logic modules that combine the functionality of two or more of the modules described hereinabove, may be used without departing from the scope of the present application.

Still referring to FIGS. 1 and 2, the data storage device 240, which may generally be a storage medium that is separate from the memory 220, may contain a data repository for storing electronic data. The data storage device 240 may be any physical storage medium, including, but not limited to, a hard disk drive (HDD), memory, removable storage, and/or the like. While the data storage device 240 is depicted as a local device in FIG. 2, it should be understood that the data storage device 240 may be a remote storage device that is remotely located from the monitoring device 110, such as, for example, a server computing device or the like.

Illustrative data that may be contained within the data storage device 240 may include, for example, image data 242 and/or other data 244. The image data 242 generally includes images that are obtained from the first imaging component 112 and/or the second imaging component 114. In some embodiments, the image data 242 may be accessible by the processing device 210 when executing processes encoded within the locating logic 226 and/or the vital determination logic 228. In some embodiments, the image data 242 may be temporarily stored within the data storage device 240 before being offloaded to an external device, being deleted, being overwritten, or the like. The other data 244 is not limited by the present disclosure, and may generally be any other data that is generated and/or stored as a result of operation of the system 100 or component thereof (such as the monitoring device 110).

The network interface hardware 230 may generally provide the monitoring device 110 with an ability to interface with one or more external components, such as, for example, an external device (e.g., user device 140), a remote server, and/or the like that is external to the monitoring device 110. Communication with external devices may occur using various communication ports (not shown). An illustrative communication port may be attached to a communications network, such as the Internet, an intranet, a local network, a direct connection, and/or the like.

It should be understood that the components illustrated in FIG. 2 are merely illustrative and are not intended to limit the scope of this disclosure. More specifically, while the components in FIG. 2 are illustrated as residing within the monitoring device 110, this is a nonlimiting example. In some embodiments, one or more of the components may reside external to the monitoring device 110. Similarly, one or more of the components may be embodied in other devices not specifically described herein.

Referring again to FIG. 1, in various embodiments, the monitoring device 110 may incorporate or be coupled to various other components to provide additional functionality. For example, in some embodiments, the monitoring device 110 may incorporate various mechanisms that allow the first imaging component 112 and/or the second imaging component 114 to move, such as to change location, pan, tilt, scan, and/or the like.

Figure 3:
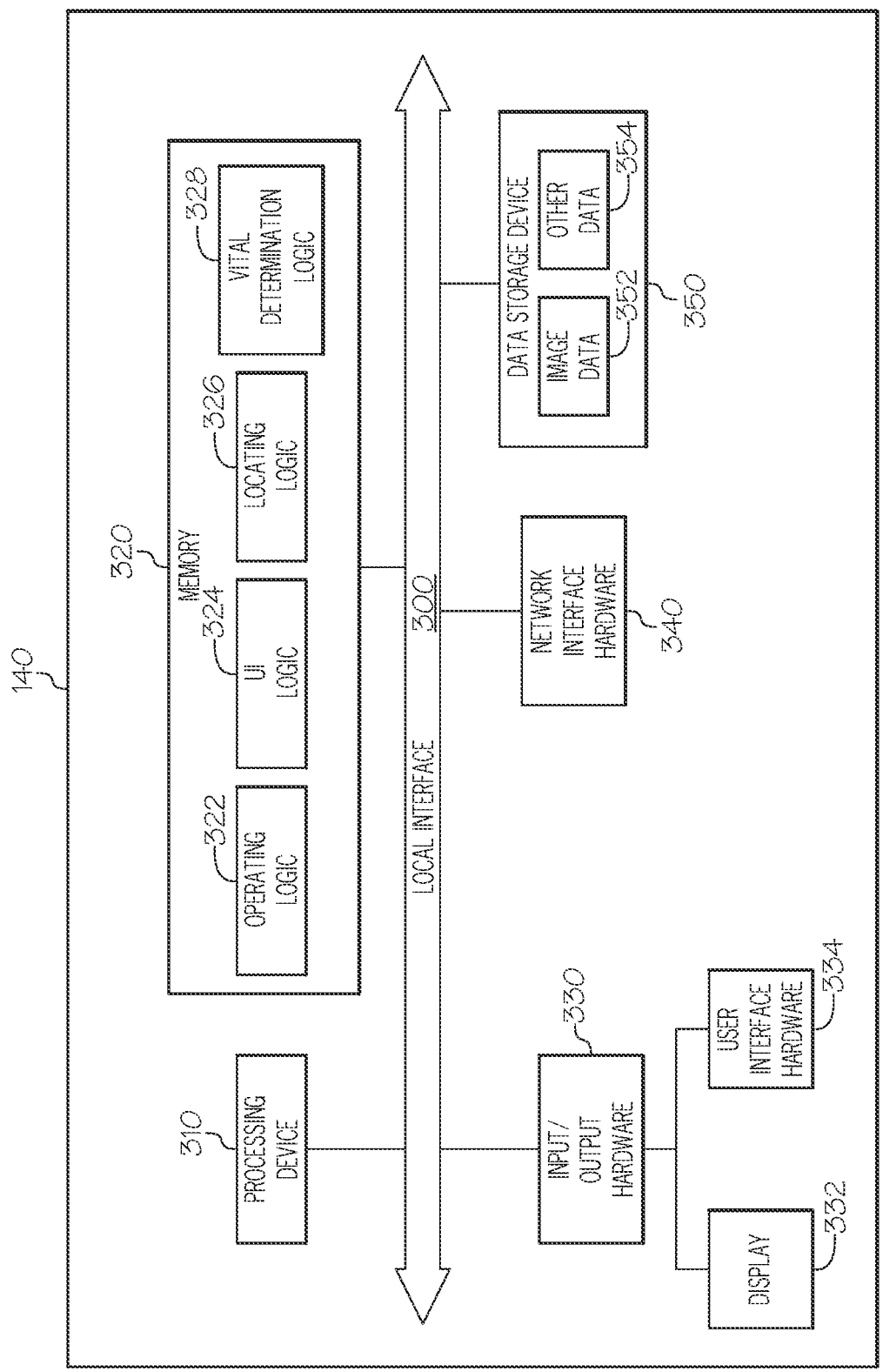
FIG. 3 schematically depicts a block diagram of illustrative internal components of a computing device within a subject monitoring system according to one or more embodiments shown or described herein.

The user device 140 may generally be any device that contains hardware that is operable to be used as an interface between a user and the other components of the system 100. Thus, the user device 140 may be used to perform one or more user-facing functions such as, for example, receiving image data and/or other data from the monitoring device 110, displaying the image data and/or other data to a user, receiving one or more user inputs, transmitting signals corresponding to the one or more user inputs, and/or the like. In addition, the user device 140 may be used to process image data and/or other data received from the monitoring device 110, as described herein. While FIG. 1 depicts the user device 140 as a smart phone, it should be understood that this is a nonlimiting example. That is, the user device 140 may be any mobile phone, a tablet computing device, a personal computing device (e.g., a personal computer), and/or the like. Illustrative internal components contained within the user device 140 are shown and described with respect to FIG. 3. As depicted in FIG. 3, the user device 140 may further include a local interface 300 (e.g., a bus) that communicatively interconnects the various components, including, but not limited to, a processing device 310, memory 320, input/output hardware 330, network interface hardware 340, and/or a data storage device 350.

The processing device 310, such as a computer processing unit (CPU), may be the central processing unit of the user device 140, performing calculations and logic operations required to execute a program. The processing device 310, alone or in conjunction with one or more of the other elements disclosed in FIG. 3, is an illustrative processing device, computing device, processor, or combination thereof, as such terms are used in this disclosure.

The memory 320, such as read only memory (ROM) and random access memory (RAM), may constitute illustrative memory devices (i.e., non-transitory, processor-readable storage media). Such memory 320 may include one or more programming instructions thereon that, when executed by the processing device 310, cause the processing device 310 to complete various processes, such as the processes described herein. Optionally, the program instructions may be stored on a tangible computer-readable medium such as a digital disk, flash memory, a memory card, a USB drive, an optical disc storage medium (e.g., Blu-ray™, CD, DVD), and/or other non-transitory processor-readable storage media.

In some embodiments, the program instructions contained on the memory 320 may be embodied as a plurality of software modules, where each module provides programming instructions for completing one or more tasks. For example, as shown in FIG. 3, the memory 320 may contain one or more of operating logic 322, user interface (UI) logic 324, locating logic 326, and vital determination logic 328. The operating logic 322 may include an operating system and/or other software for managing components of the user device 140. The UI logic 324 may generally include programming instructions for interacting with a user via a user interface. That is, the UI logic 324 may provide instructions for the processing device 310 to complete particular processes as the result of particular user inputs and/or transmit information and/or data to the user via a user interface, as described in greater detail herein. Referring to FIGS. 1 and 3, the locating logic 326 may generally include programming instructions for determining a location of the subject S on the surface 132 of the patient support apparatus 130 based on images received from the first imaging component 112 and/or the second imaging component 114. The vital determination logic 328 may generally include programming instructions for determining vital signs of the subject S, including a body temperature (e.g., a facial temperature), a heart rate, and/or a respiration rate of the subject S, based on the images received from the first imaging component 112 and/or the second imaging component 114. It should be understood that the locating logic 326 and/or the vital determination logic 328 of the memory 320 of the user device 140 may provide programming and/or instructions that is similar to the programming and/or instructions provided by the locating logic 226 and/or the vital determination logic 228 of the memory 220 of the monitoring device 110 depicted in FIG. 2. As such, the locating logic 326 and/or the vital determination logic 328 of the memory 320 of the user device 140 may be used in lieu of the locating logic 226 and/or the vital determination logic 228 of the memory 220 of the monitoring device 110 depicted in FIG. 2 in some embodiments or may be used in conjunction with the locating logic 226 and/or the vital determination logic 228 of the memory 220 of the monitoring device 110. It should be understood that the various logic modules described herein with respect to FIG. 3 are merely illustrative, and that other logic modules, including logic modules that combine the functionality of two or more of the modules described hereinabove, may be used without departing from the scope of the present application.

Still referring to FIGS. 1 and 3, the data storage device 350, which may generally be a storage medium that is separate from the memory 320, may contain a data repository for storing electronic data. The data storage device 350 may be any physical storage medium, including, but not limited to, a hard disk drive (HDD), memory, removable storage, and/or the like. While the data storage device 350 is depicted as a local device in FIG. 3, it should be understood that the data storage device 350 may be a remote storage device that is remotely located from the monitoring device 110, such as, for example, a server computing device or the like.

Illustrative data that may be contained within the data storage device 350 may include, for example, image data 352 and/or other data 354. The image data 352 generally includes images that are obtained from the first imaging component 112 and/or the second imaging component 114. In some embodiments, the image data 352 may be accessible by the processing device 310 when executing processes encoded within the locating logic 326 and/or the vital determination logic 328. In some embodiments, the image data 352 may be temporarily stored within the data storage device 350 before being offloaded to an external device, being deleted, being overwritten, or the like. The other data 354 is not limited by the present disclosure, and may generally be any other data that is generated and/or stored as a result of operation of the system 100 or component thereof (such as the monitoring device 110 and/or the user device 140).

The input/output hardware 330 may generally include hardware that is used to provide an interface between one or more user interface devices or components and the various internal components of the user device 140 depicted in FIG. 3. For example, in the embodiment depicted in FIG. 3, the input/output hardware 330 may be communicatively coupled to a display 332 and/or user interface hardware 334. The input/output hardware 330 may permit information from the local interface 300 to be displayed on the display 332 in audio, visual, graphic, or alphanumeric format in some embodiments. The user interface hardware 334 may allow for transmission to and receipt of data from input devices such as a keyboard, a mouse, a joystick, a touchscreen, a remote control, a pointing device, a video input device, an audio input device, a haptic feedback device, and/or the like. In some embodiments, particularly embodiments where the user device 140 is a device having a touchscreen display, such as a smartphone, a tablet computing device, or the like, the display 332 and the user interface hardware 334 may be integrated into a single component.

The network interface hardware 340 may generally provide the user device 140 with an ability to interface with one or more external components, such as, for example, an external device (e.g., the monitoring device 110), a remote server, and/or the like that is external to the user device 140. Communication with external devices may occur using various communication ports (not shown). An illustrative communication port may be attached to a communications network, such as the Internet, an intranet, a local network, a direct connection, and/or the like.

It should be understood that the components illustrated in FIG. 3 are merely illustrative and are not intended to limit the scope of this disclosure. More specifically, while the components in FIG. 3 are illustrated as residing within the user device 140, this is a nonlimiting example. In some embodiments, one or more of the components may reside external to the user device 140. Similarly, one or more of the components may be embodied in other devices not specifically described herein.

Referring again to FIG. 1, various components of the system 100 may generally be located in a room or an area that is used for subject care. For example, in some embodiments, certain components of the system 100 may be located in an operating room, a surgical suite, a recovery room, a subject's room, or the like. In some embodiments, all of the components of the system 100 may be located in the same room or area. In other embodiments, certain components of the system 100 may be remotely located. In a nonlimiting example, the user device 140 and/or one or more components thereof may be remotely located (e.g., not located in the same room or space as the monitoring device 110. For example, the user device 140 may be a remotely located server that is communicatively coupled to the monitoring device 110.

Figure 4:
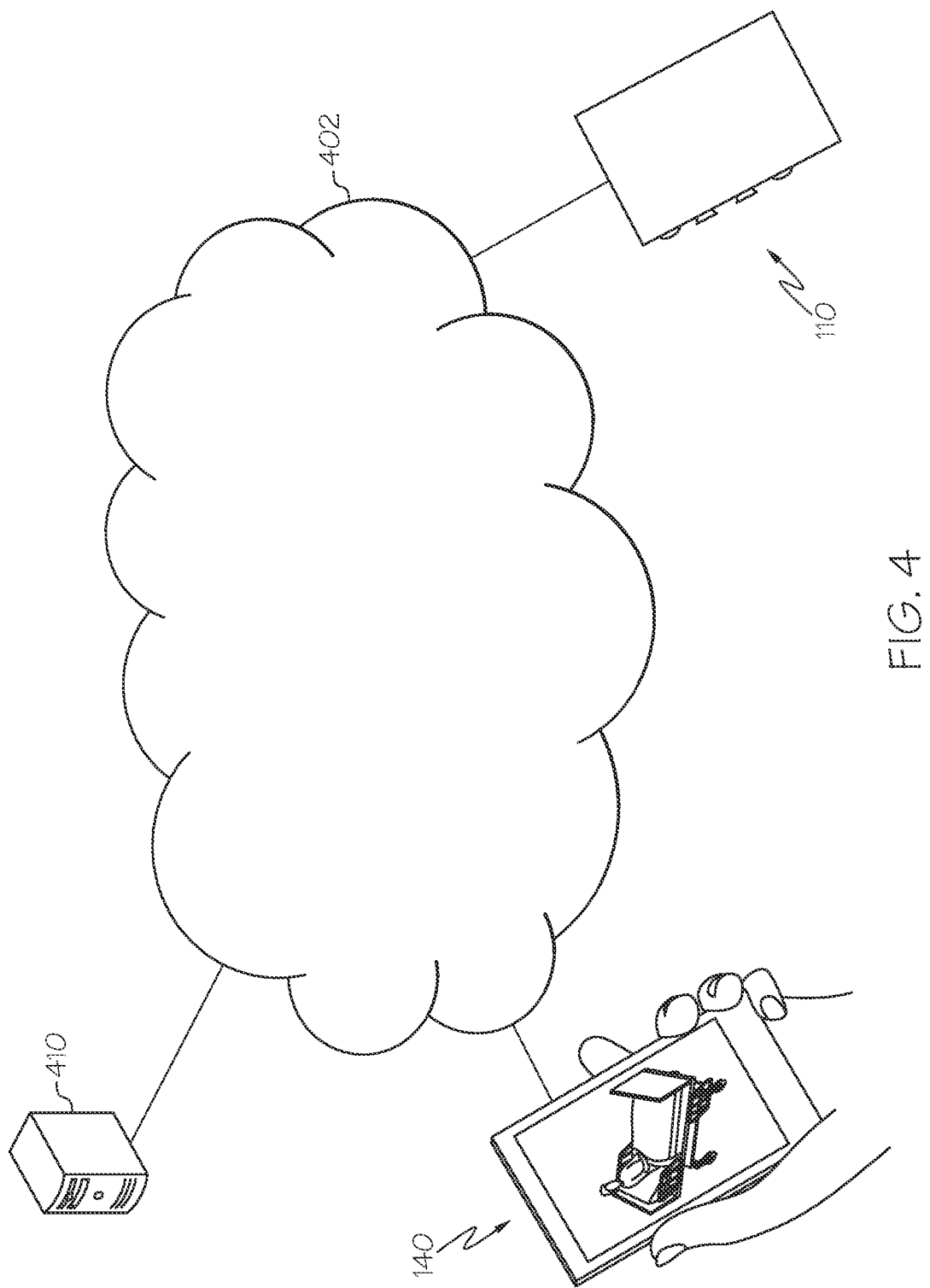
FIG. 4 schematically depicts interconnectivity between components of an illustrative subject monitoring network according to one or more embodiments shown or described herein.

Certain components of the system 100 are communicatively coupled to each other to transmit data. For example, as depicted in FIG. 4, a subject monitoring network 400 may be used to communicatively couple one or more components together. The subject monitoring network 400 may include a wide area network (WAN), such as the Internet, a local area network (LAN), a mobile communications network, a public service telephone network (PSTN), a personal area network (PAN), a metropolitan area network (MAN), a virtual private network (VPN), and/or another network. The subject monitoring network 400 may generally be configured to electronically connect one or more devices such as computing devices and/or components thereof. Illustrative devices may include, but are not limited to, the monitoring device 110, the user device 140, and/or a server computing device 410.

The server computing device 410 may receive data from one or more sources (e.g., the user device 140 and/or the monitoring device 110), analyze received data (e.g., determine a subject's head position, determine a subject's location relative to the patient support apparatus, determine a subject's facial temperature, determine a subject's heart rate, determine a subject's respiration rate, and/or the like), generate data, store data, index data, search data, and/or provide data to the user device 140 and/or the monitoring device 110. In some embodiments, the server computing device 410 may analyze received data in conjunction with analysis steps completed by the user device 140 and/or the monitoring device 110. In other embodiments, the server computing device 410 may analyze received data in lieu of any analysis that may be completed by the user device 140 and/or the monitoring device 110.

It should be understood that while the server computing device 410 is depicted as a server, this is a nonlimiting example. In some embodiments, any type of computing device (e.g., mobile computing device, personal computer, server, cloud-based network of devices, etc.) may be used. Additionally, while each of these computing devices is illustrated in FIG. 4 as a single piece of hardware, this is also merely an example. The server computing device 410 may represent a plurality of computers, servers, databases, components, and/or the like.

Figure 5:
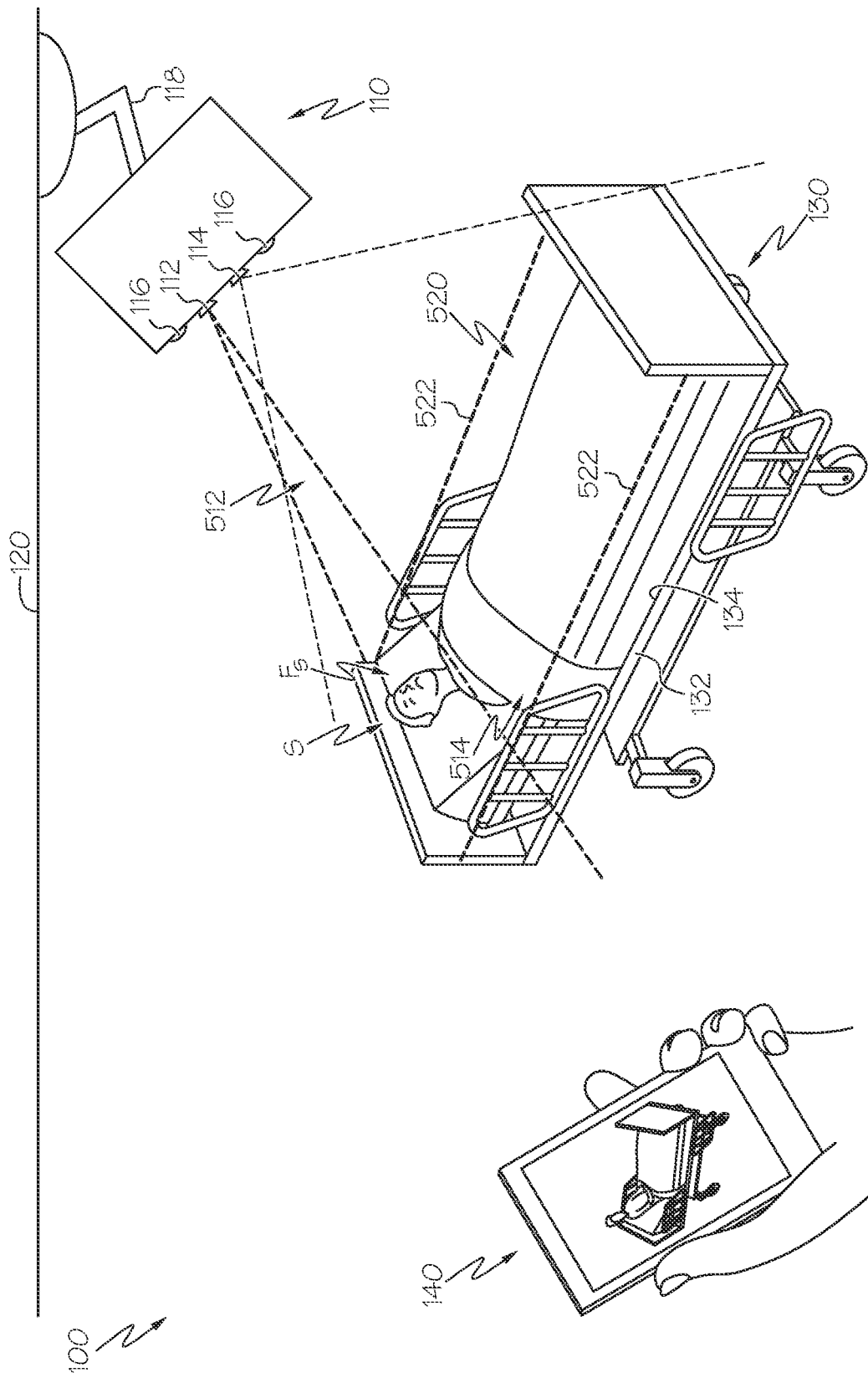
FIG. 5 schematically depicts operation of an illustrative subject monitoring system to monitor subject positioning according to one or more embodiments shown or described herein.

Referring now to FIG. 5, the user device 140 and/or one or more components thereof are arranged such that one or more images are received from the monitoring device 110 and/or information and one or more images are displayed to a user, such as, for example, various personnel that are caring for the subject S. Thus, at least one component of the user device 140 (such as a display) may be arranged such that the user can view the displayed images.

Referring to FIGS. 5 and 6A-6D, the monitoring device 110 monitors a positioning of the subject S with respect to the patient support apparatus 130 to determine whether the subject S is laying in the patient support apparatus (as depicted in image 600 in FIG. 6A), sitting up in the patient support apparatus 130 (as depicted in image 600 in FIG. 6B), completely off the patient support apparatus 130 (as depicted in image 600 in FIG. 6C), sitting on an edge of the patient support apparatus 130 (as depicted in image 600 in FIG. 6D), and/or the like. This is generally completed by utilizing the first imaging component 112 to obtain thermal image data of the subject's face $F_S$ and utilizing the second imaging component 114 to obtain additional image data of the patient support apparatus 130 so as to determine the boundaries 134 of the patient support apparatus 130 and construct a virtual boundary 522 that corresponds to the boundaries 134 of the patient support apparatus 130. That is, the first imaging component 112 is positioned such that the subject's face $F_S$ is located within a first field of view 512 of the first imaging component 112, as delineated by the dashed lines extending from the first imaging component 112 in FIG. 5. In addition, the second imaging component 114 is positioned such that the surface 132 of the patient support apparatus 130 is located within a second field of view 514 of the second imaging component 114, as delineated by the dashed lines extending from the second imaging component 114 in FIG. 5.

Still referring to FIGS. 5 and 6A-6D, the subject's face $F_S$ may generally be determined by receiving the thermal image data from the first imaging component 112 and utilizing any facial recognition algorithm now known or later developed to determine, from the thermal image data, a particular arrangement and color of pixels that corresponds to a shape, size, and temperature of a face. That is, a facial recognition algorithm may analyze an arrangement of pixels to determine an object that generally corresponds to the dimensions of a known face shape and/or size, and may further analyze a color of pixels to determine a color that generally corresponds to a body temperature of a human (e.g., generally about 37 degrees Celsius, but with some variation to account for individuals exhibiting hypothermia, hyperthermia, or pyrexia conditions). In some embodiments, additional data may be obtained from the image data received from the second imaging component 114 to more accurately determine whether a particular arrangement of pixels in the images received from the first imaging component 112 correspond to stored characteristics of possible face shapes and sizes. That is, the monitoring device 110 may analyze image data received from the second imaging component 114 to more accurately discern particular boundaries of an object, and then use the particular boundaries in conjunction with the image data from the first imaging component 112 to determine whether the object corresponds to stored face dimensions.

The boundaries 134 of the patient support apparatus 130 may generally be determined by receiving the image data from the second imaging component 114 and analyzing the image data for objects that correspond to known shapes and sizes of patient support apparatuses. That is, an object recognition algorithm that is now known or later developed may be utilized to analyze the image data received from the first imaging component 112, determine object within the image data, determine a shape and/or size of the objects, and determine whether the shape and/or size corresponds to a known shape and/or size of a patient support apparatus or other surface. For example, if the image data includes an object that is generally rectangular in shape, is about one (1) meter wide, and is about two (2) meters long, a determination may be made that the object is a patient support apparatus. Once such a determination is made, the monitoring device 110 constructs the virtual boundary 522 around the object in the image 600 generated from the image data, the virtual boundary 522 corresponding to the boundaries 134 of the patient support apparatus 130. As such, the virtual boundary 522 generally has the same shape and size as the boundaries 134 of the patient support apparatus 130, as depicted in FIGS. 5 and 6A-6D. The virtual boundaries 522 form a monitored area 520 that is used to determine whether the subject S is in the patient support apparatus 130 and/or how the subject S is positioned in the patient support apparatus 130.

In some embodiments, particularly embodiments where the patient support apparatus 130 is in a darkened room, it may be difficult to obtain sufficient RGB images from the second imaging component 114 to accurately determine the patient support apparatus 130, the subject S, and/or the like and construct accurate virtual boundaries 522. In such embodiments, the one or more light emitting components 116 may be activated to emit NIR light that, while not detectable by the human eye (room still appears to be darkened to the human eye), the patient support apparatus 130 and the subject S are adequately illuminated with NIR light that can be imaged by the NIR sensors in the second imaging component 114 to produce an image that is sufficient for the purposes of determining the patient support apparatus 130, the subject S, and/or the like and to construct the virtual boundaries 522.

Once the subject's face $F_S$ has been detected using the facial recognition algorithm and the virtual boundaries 522 are overlaid on the image 600 generated from the image data received from the first imaging component 112 and/or the second imaging component 114, the monitoring device 110 may assign a particular point that is generally located at the detected face in the image 600 and determine the coordinates of the particular point with respect to the virtual boundaries 522. For example, as shown in FIG. 6A and FIG. 7A, a point P located in the middle of the face displayed on the image 600 of the subject S is selected, and the x,y coordinates of the point P with respect to the virtual boundaries 522 is determined. That is, the x coordinate may correspond to a number of units (e.g., pixels in the image 600) from the virtual boundary 522 corresponding to the left side of the patient support apparatus 130 to point P. In addition, the y coordinate may correspond to a number of units (e.g., pixels in the image 600) from the virtual boundary 522 corresponding to the head portion of the patient support apparatus 130 to point P. The x,y coordinates of the point P on the subject's head may be provided within an interface 700 that is displayed to a user. The color of the pixel(s) and/or any other distinguishing characteristics at point P that may be used to identify an object in the image 600 that exists at point P at the time of an initial imaging (e.g., shape and/or size of an object) may be recorded such that point P is stored as a reference in memory.

Referring to FIGS. 5, 6A-6D, and 7A-7F, the respective image data received from the first imaging component 112 and the second imaging component 114 may be stitched together and/or overlaid to obtain a composite image that is displayed within the interface 700 for the purposes of subsequently tracking movement of the subject S. For example, image 600*a* in the upper left corner of the interface 700 depicted in FIG. 7A shows only image data from the second imaging component 114 (e.g., NIR image data and/or RGB image data). Image 600*b* in the upper right corner of the interface 700 depicted in FIG. 7A shows a composite formed from image data from both the first imaging component 112 (e.g., thermal image data) and the second imaging component 114 (e.g., NIR image data and/or RGB image data). Image 600*c* in the lower middle of the interface 700 depicted in FIG. 7A shows only image data from the first imaging component 112 (e.g., thermal image data). Further, as depicted in FIGS. 7A-7F, a head-tracking virtual boundary 702 may be drawn around the subject's head Hs to assist with further tracking movement of the subject S. Accordingly, the characteristics of point P can be accessed thereafter for the purposes of determining whether the subject's head Hs has moved in subsequent image data that is received from the first imaging component 112 and/or the second imaging component 114. That is, the location of point P is continually tracked as the subject S moves, as determined from subsequent image data received from the first imaging component 112 and/or the second imaging component 114. That is, the subsequently received image data may be further analyzed by one or more image processing algorithms (e.g., a facial recognition algorithm, an object recognition algorithm, and/or the like) to determine an updated positioning of the subject S. As shown in FIGS. 7A-7F, the interface 700 is updated whenever a new location of point P is detected, with the coordinates displayed within the interface under the images. In addition, the determination of whether the subject S is in the patient support apparatus 130 is made based on the location of the virtual boundary 522 and the coordinates corresponding to point P. For example, as shown in FIG. 7F, the coordinates (−28,−5) of point P indicate that the subject S is no longer in the patient support apparatus 130, and thus a determination is made that the subject S is out of the patient support apparatus 130, which is displayed in the interface 700.

Still referring to FIGS. 5, 6A-6D, and 7A-7F, the system 100 is further configured such that a user of the user device 140 may access up-to-date images 600 from the monitoring device 110 to check in on the status of the subject S at any time. In addition, the user of the user device 140 may receive alerts from the monitoring device 110 any time a preset condition occurs with respect to the positioning of the subject S. For example, if the subject S sits up in the patient support apparatus (as depicted in image 600 in FIG. 6B), moves out of the patient support apparatus (as depicted in image 600 in FIG. 6C, or sits on an edge of the patient support apparatus (as depicted in image 600 in FIG. 6D), the monitoring device 110, upon detecting the user movement as described above, may transmit an alert to the user device 140.

Figure 8:
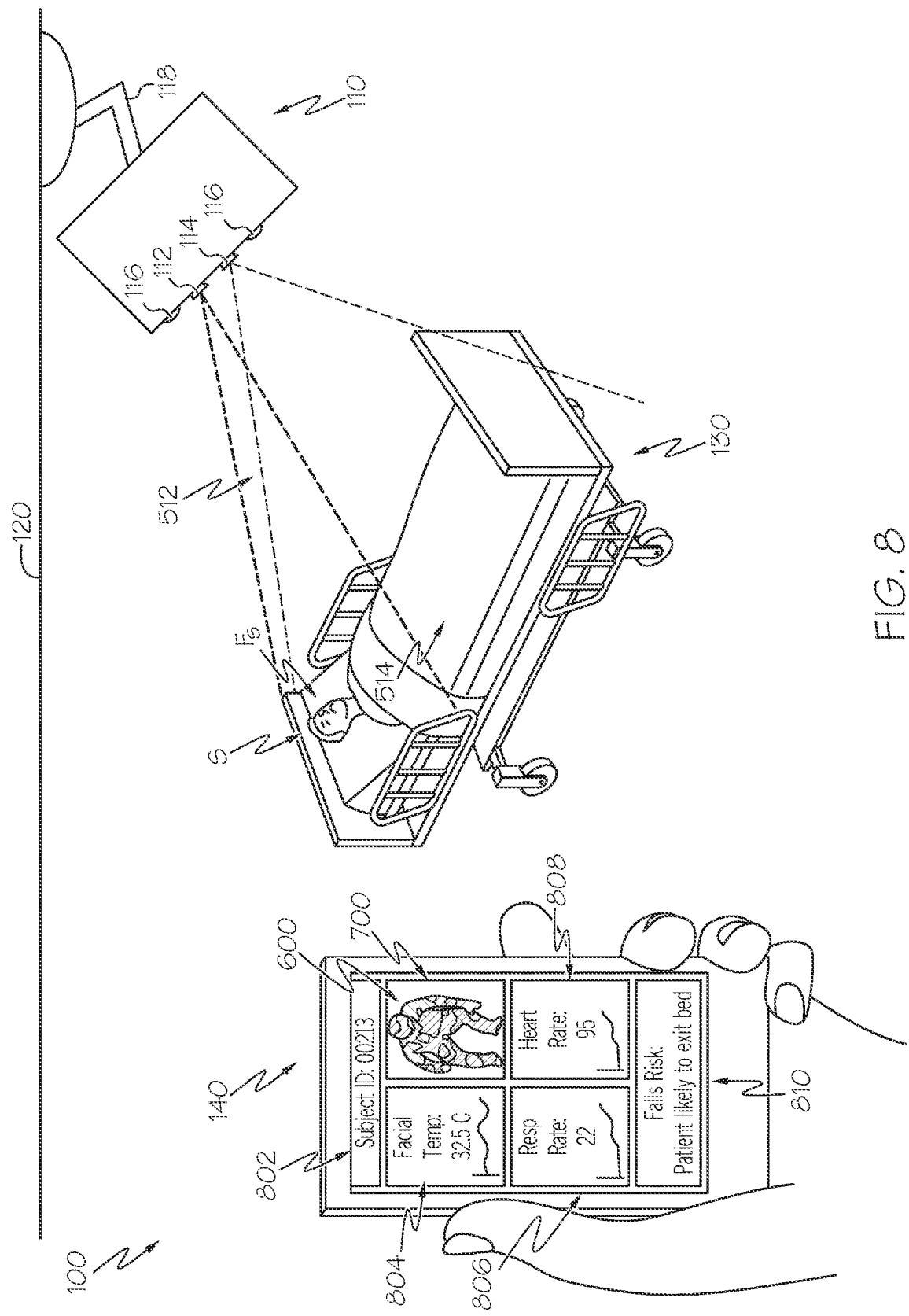
FIG. 8 schematically depicts operation of an illustrative subject monitoring system to monitor subject temperature, heart rate, and respiration rate according to one or more embodiments shown or described herein.

Referring now to FIG. 8, the user device 140 and/or one or more components thereof are arranged such that the image 600 received from the monitoring device 110 is displayed on the interface 700, along with various other information that can be used by a user. Illustrative examples of other information include, but are not limited to, a subject identifier 802, a facial temperature display 804, a respiration rate display 806, a heart rate display 808, and/or an additional information display 810 that provides additional information regarding the subject S.

The information that is provided on the user device 140 via the interface is received from the monitoring device 110, as described herein. That is, the monitoring device 110 monitors various characteristics of the subject S to provide information such as facial temperature, heart rate, and respiration rate. This is generally completed by utilizing the first imaging component 112 to obtain thermal image data of at least the subject's face $F_S$ and utilizing the second imaging component 114 to obtain additional image data of the subject S when in the patient support apparatus 130. That is, the first imaging component 112 is positioned such that at least the subject's face $F_S$ is located within the first field of view 512 of the first imaging component 112, as delineated by the dashed lines extending from the first imaging component 112 in FIG. 8. In addition, the second imaging component 114 is positioned such that at least a portion of the subject S is located within the second field of view 514 of the second imaging component 114, as delineated by the dashed lines extending from the second imaging component 114 in FIG. 8.

As will be described in greater detail herein, the facial temperature of the subject is generally determined by obtaining image data from the first imaging component 112 (e.g., thermal image data) and determining the temperature of the subject's face $F_S$ from the image data based on the colors of the pixels in the area determined to encompass the subject's face $F_S$, as described herein. In some embodiments, the facial temperature may be determined from a particular point on the subject's face $F_S$. In other embodiments, the facial temperature may be determined from an average facial temperature of the subject's face $F_S$. That is, the temperature is determined from a plurality of pixels located at various locations in the image data that correspond to the subject's face $F_S$ and all of the determined temperatures are averaged together to obtain the average facial temperature. It should be understood that a determination of facial temperature is frequently used to correlate to body temperature.

A respiration rate of the subject S can be determined from the image data received from the first imaging component 112 and/or the second imaging component 114. That is, the chest movements of the subject S are obtained from the image data, and the chest movements are used to determine a respiration rate. For example, image data containing several successive images that are obtained over a period of time (e.g., a video stream) may be obtained from the first imaging component 112 and/or the second imaging component 114. Using the object recognition algorithms and methods previously discussed herein, an expansion and contraction of the chest of the subject S can be detected from the video stream, and using the speed of image capture (e.g., frames per second), an amount of time in which the chest of the subject S moves through an expansion/contraction cycle can be determined and used to calculate the number of respirations per minute (e.g., number of expansion/contraction cycles that occur in a minute). The respiration rate may be continuously determined and calculated such that the respiration rate provided to the user device 140 is up-to-date.

Figure 9A:
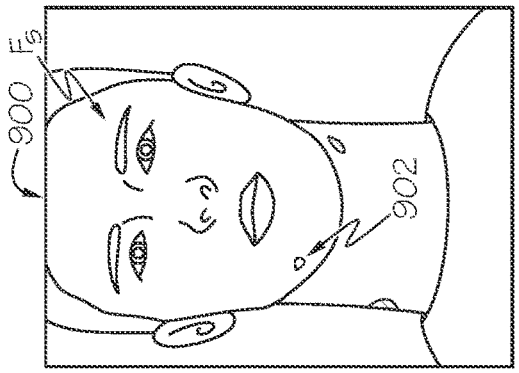
FIG. 9A schematically depicts an illustrative screen shot of an image obtained by a monitoring device for the purposes of determining heart rate according to one or more embodiments shown or described herein.
Figure 9B:
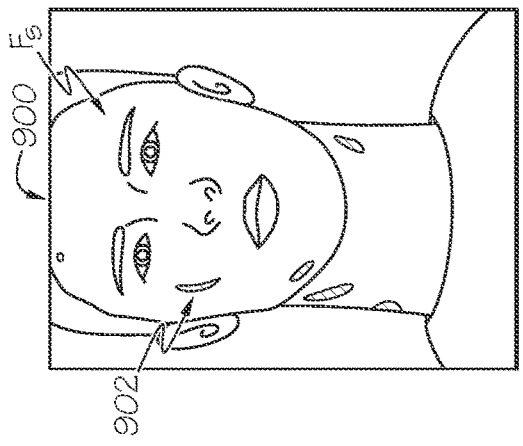
FIG. 9B schematically depicts another illustrative screen shot of an image obtained by a monitoring device for the purposes of determining heart rate according to one or more embodiments shown or described herein FIG. 9C schematically depicts another illustrative screen shot of an image obtained by a monitoring device for the purposes of determining heart rate according to one or more embodiments shown or described herein.
Figure 9C:
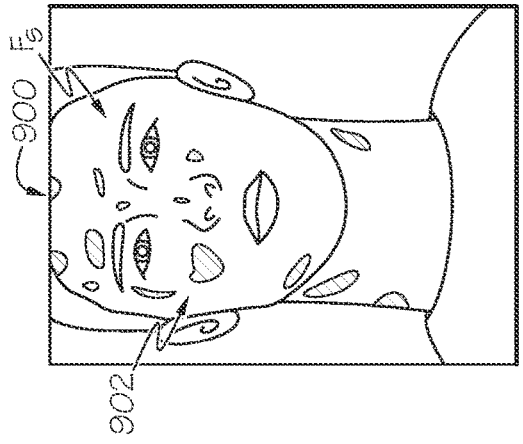
FIG. 9D schematically depicts another illustrative screen shot of an image obtained by a monitoring device for the purposes of determining heart rate according to one or more embodiments shown or described herein.
FIG. 9E schematically depicts another illustrative screen shot of an image obtained by a monitoring device for the purposes of determining heart rate according to one or more embodiments shown or described herein.
FIG. 9F schematically depicts another illustrative screen shot of an image obtained by a monitoring device for the purposes of determining heart rate according to one or more embodiments shown or described herein.
Figure 9D:
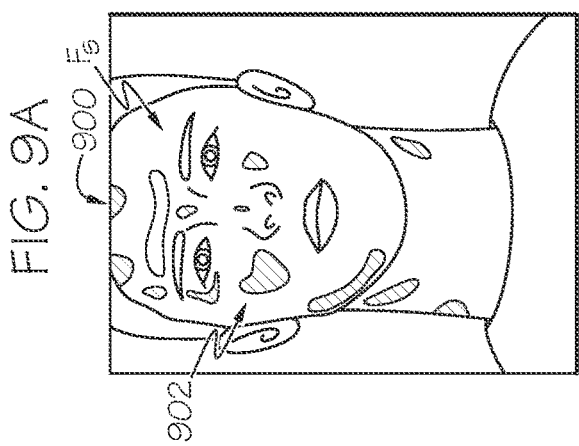
Figure 9E:
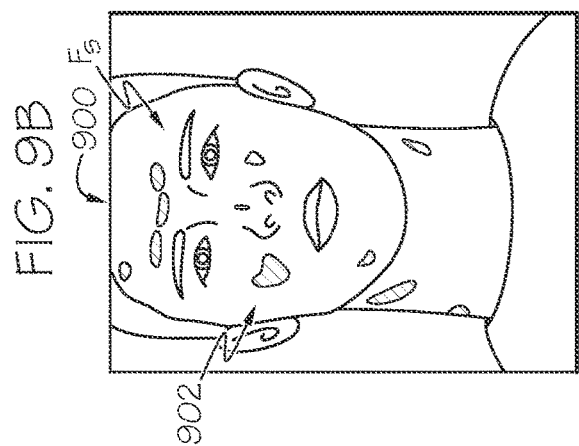
Figure 9F:
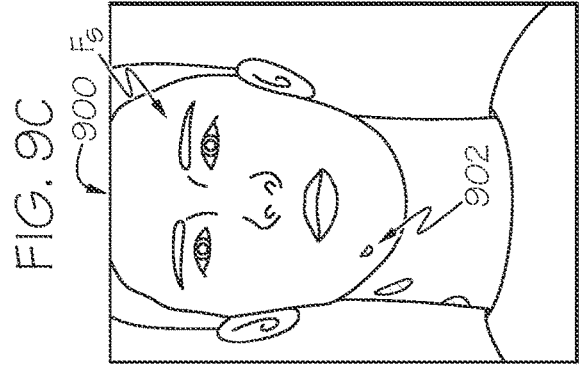

A heart rate of the subject S may generally be determined by analyzing image data received from the second imaging component 114 and applying a coded hemodynamic imaging (CHI) technique. More specifically, NIR light that is projected onto the subject's face $F_S$ by the one or more light emitting components 116 is partially absorbed by the influx of partially oxygenated blood in the skin capillaries at each heartbeat. As such, the remaining NIR light that is reflected and detected by the second imaging component 114 varies based on how much blood has absorbed the NIR light. For example, as shown in FIGS. 9A-9F, the amount of absorbed NIR light 902 that appears in each image 900 when captured by the second imaging component 114 varies based on the amount of partially oxygenated blood present in the capillaries of the subject's face $F_S$. More specifically, FIGS. 9A-9F depict a fluctuation in the amount of oxygenated blood in the capillaries of the subject's face $F_S$ through the course of one cardiac cycle. As shown in FIG. 9A, fewer areas of absorbed NIR light 902 are shown, which indicates that less oxygenated blood is present in the capillaries, which further indicates that the heart is in the diastole phase (blood is entering the heart). FIG. 9B depicts more areas of absorbed NIR light 902 and FIG. 9C depicts even more areas of absorbed NIR light 902, which indicates an increasing amount of oxygenated blood present in the capillaries, which further indicates that the heart is in the systole phase (pumping the blood out of the heart). As the heart then cycles back into the diastole phase, the number of areas of absorbed NIR light 902 on the subject's face $F_S$ decreases, as shown in the progression from FIG. 9D to FIG. 9E and then to FIG. 9F. Referring to FIGS. 8 and 9A-9F, the monitoring device 110 may use one or more image processing algorithms to determine an amount of oxygenated blood in the subject's face $F_S$ based on the amount of absorbed NIR light 902 and determine when a cardiac cycle occurs based on the fluctuation shown and described in FIGS. 9A-9F. In addition, the monitoring device 110 may receive data from the second imaging component 114 regarding the speed of image capture (e.g., number of frames per second) to determine an amount of time in which the subject S progresses through a cardiac cycle to determine the heart rate of the subject S (e.g., beats per minute). The heart rate may be continuously determined and calculated such that the heart rate provided via the user device 140 is up-to-date.

The various processes described with respect to FIGS. 5, 6A-6D, 7A-7F, 8, and 9A-9D that may be carried out by the monitoring device 110 in obtaining image data from the first imaging component 112 and/or the second imaging component 114, determining subject positioning and/or movement, determining subject temperature, determining subject respiration rate, determining subject heart rate, and providing information and/or images to the user device 140 may be completed according to the processes described in FIGS. 10-14. Each of the processes described with respect to FIG. 10-14 may be embodied by one or more programmed instructions stored on one or more memory devices, such as the memory 220 of the monitoring device 110 (FIG. 2) and/or the memory 320 of the user device 140 (FIG. 3) described herein.

Figure 10:
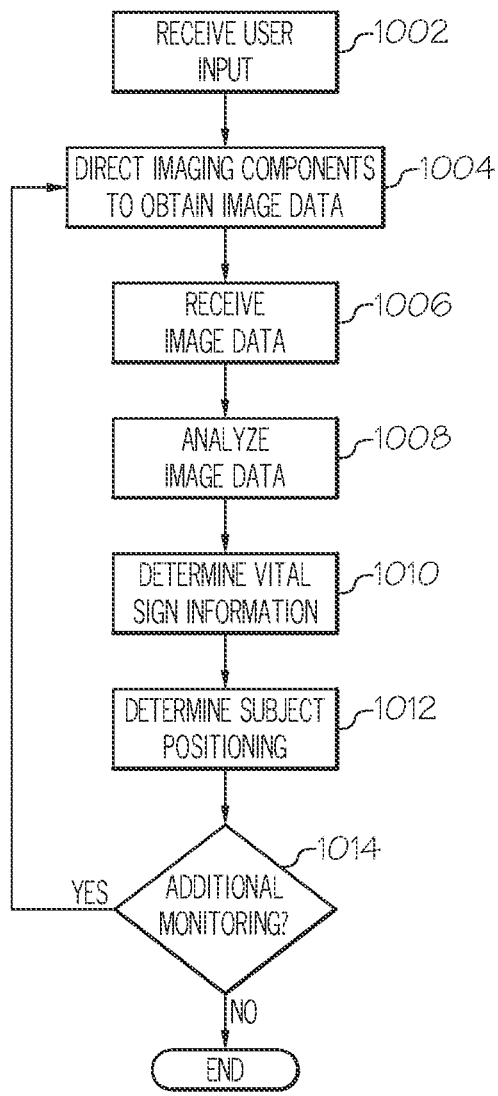
FIG. 10 depicts a flow diagram of an illustrative overview method of concurrently determining a subject positioning, temperature, heart rate, and respiration rate using a subject monitoring system according to one or more embodiments shown or described herein.

FIG. 10 depicts an overview method of concurrently determining subject positioning, movement, and vital signs (e.g., temperature, respiration rate, and heart rate) according to an embodiment. Referring to FIGS. 1, 2, 3, and 10, at block 1002, the processing device 210 of the monitoring device 110 or the processing device 310 of the user device 140 may receive a user input to begin determining subject positioning, movement, and vital signs. It should be understood that the process according to block 1002 is optional. That is, in some embodiments, the processing device 210 of the monitoring device 110 and/or the processing device 310 of the user device 140 may not receive a user input to begin determining subject positioning, movement, and vital signs. For example, the processing device 210 may recognize, based on constantly received image data received from the imaging components 112, 114 when the subject S and the patient support apparatus 130 are within the field of view of the first imaging component 112 and/or the second imaging component 114 and begin determining positioning, movement, and vital signs, or the monitoring device 110 may be in an "always on" state when powered on such that the monitoring device and/or components thereof are ready to complete the various processes described with respect to FIG. 10 without any user input.

Referring to FIGS. 1, 2, and 10, in some embodiments, the processing device 210 may direct the first imaging component 112 and/or the second imaging component 114 to obtain image data (e.g., thermal image data, RGB image data, and/or NIR image data) at block 1004. For example, the processing device 210 may direct the first imaging component 112 and/or the second imaging component 114 by transmitting a signal to the first imaging component 112 and/or the second imaging component 114. It should be understood that the process according to block 1004 is optional. That is, in some embodiments, the first imaging component 112 and/or the second imaging component 114 may obtain image data and/or transmit data without direction from the processing device 210 or a component thereof. For example, the first imaging component 112 and/or the second imaging component 114 may automatically obtain image data and/or transmit data when powered on.

At block 1006, the processing device 210 receives the image data from the first imaging component 112 and/or the second imaging component 114. The processing device 210 analyzes the image data at block 1008. The image data is generally analyzed for the purposes of determining a positioning and/or a movement of the subject S, constructing virtual boundaries that correspond to the boundaries 134 of the patient support apparatus 130, determining a facial temperature of the subject's face $F_S$, determining a respiration rate of the subject S, and determining a heart rate of the subject S, as described in greater detail herein. Accordingly at block 1010, the processing device 210 determines vital sign information from the received image data. That is, the processing device 210 determines a facial temperature of the subject S, determines a heart rate of the subject S, and determines a respiration rate of the subject S at block 1010. However, it should be understood that the processing device 210 may further determine other vital signs from the image data in some embodiments without departing from the scope of the present disclosure. In addition, the processing device 210 determines a positioning of the subject S with respect to the patient support apparatus 130 at block 1012. That is, the processing device 210 utilizes facial recognition algorithms and/or object recognition algorithms as described herein to determine objects in the image data corresponding to the subject S, including the subject's face $F_S$.

As previously discussed herein, the monitoring device 110 may continuously monitor the subject for positioning, movement, and vital signs by receiving a constant stream of image data (e.g., a video feed) from the first imaging component 112 and/or the second imaging component 114. Accordingly, the processing device 210 determines whether additional monitoring of the subject S is necessary at block 1014. Such a determination may generally be based on one or more inputs received from a user, whether a subject S is in the patient support apparatus 130 (e.g., within the field of view of the first imaging component 112 and/or the second imaging component 114), and/or the like. For example, in some embodiments, a user may wish to continuously monitor a subject S in the patient support apparatus indefinitely. In such instances, the processing device 210 may receive an input that indicates that additional monitoring should continuously occur or the processing device 210 may automatically be programmed to conduct additional monitoring. Additional monitoring may be necessary to track further movement and/or positioning of the subject S to determine whether the subject S has moved off the patient support apparatus 130, has sat up in the patient support apparatus 130, and/or the like. In such instances, the processing device 210 may receive an input that indicates that additional monitoring should be completed, such as, for example, an input from a user via the user device 140 indicating that the subject S is arranged in a baseline positioning or an input from a user requesting continuous monitoring.

If additional monitoring is necessary (e.g., to continuously monitor the subject S), the process returns to block 1004 to direct the first imaging component 112 and/or the second imaging component 114 to obtain additional image data. In embodiments where block 1004 is omitted, the process may return to block 1006 to receive additional image data from the first imaging component 112 and/or the second imaging component 114. If no additional monitoring is necessary, the process may end.

Figure 11:
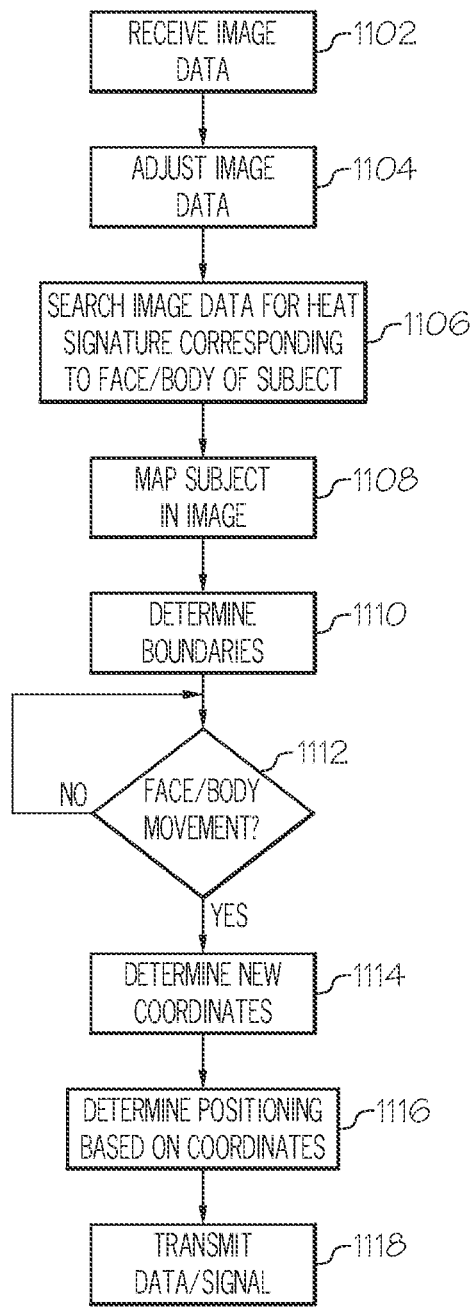
FIG. 11 depicts a flow diagram of an illustrative method of determining a subject positioning using a subject monitoring system according to one or more embodiments shown or described herein.

FIG. 11 depicts additional detail regarding a method of determining a positioning of the subject S. Referring to FIGS. 1, 2, and 11, the processing device 210 receives image data at block 1102. That is, the first imaging component 112 and/or the second imaging component 114 provide image data that is received by the processing device 210. At block 1104, the processing device adjusts the image data that is received such that the subject S can be adequately discerned for the purposes of determining location and movement. For example, the image data may be adjusted by stitching or otherwise combining first image data from the first imaging component 112 and second image data from the second imaging component 114 to obtain a composite image that includes RGB image data relating to the shapes of objects in the field of view of the second imaging component 114 and thermal image data relating to an amount of thermal radiation given off by the subject S and/or other surrounding objects. In another example, the processing device 210 may adjust the sensitivity, color, and/or the like of the image data so as to produce images that depict the subject S. Other means of adjusting the image data should generally be understood.

At block 1106, the processing device 210 searches the image data for a heat signature that corresponds to the face $F_S$ and/or body of the subject S and maps the subject in the image accordingly at block 1108. As described herein, such searching and mapping processes described with respect to blocks 1106 and 1108 may generally be completed as part of using a facial recognition algorithm and/or a shape recognition algorithm to determine the outline of the subject S within the image data. At block 1110, the boundaries 134 of the patient support apparatus 130 are determined, as described herein. As also described herein, virtual boundaries are placed over the boundaries 134 of the patient support apparatus 130 within the image data.

At block 1112, a determination is made as to whether face and/or body movement is detected. That is, if the point P as discussed herein with respect to FIGS. 6A-6D and 7A-7F moves such that the coordinates of point P change, the determination may be at block 1112 that the subject's face $F_S$ has moved. If no movement has been detected, the process may return to block 1112 until movement is detected. If movement is detected, the process may proceed to block 1114.

At block 1114, the new coordinates of the point P (FIGS. 6A-6D and 7A-7F) of the subject's face $F_S$ is determined (or coordinates of another reference point located on the subject's body). The positioning of the subject S (including the subject's face $F_S$) is determined at block 1116, as described in greater detail hereinabove. Data and/or a signal corresponding to the movement of the subject S is then transmitted at block 1118. For example, image data containing the new positioning of the subject S may be transmitted to the user device 140 and/or the server computing device 410

(FIG. 4), an alert signal may be transmitted to the user device 140 to alert a user of subject S movement, and/or the like.

Figure 12:
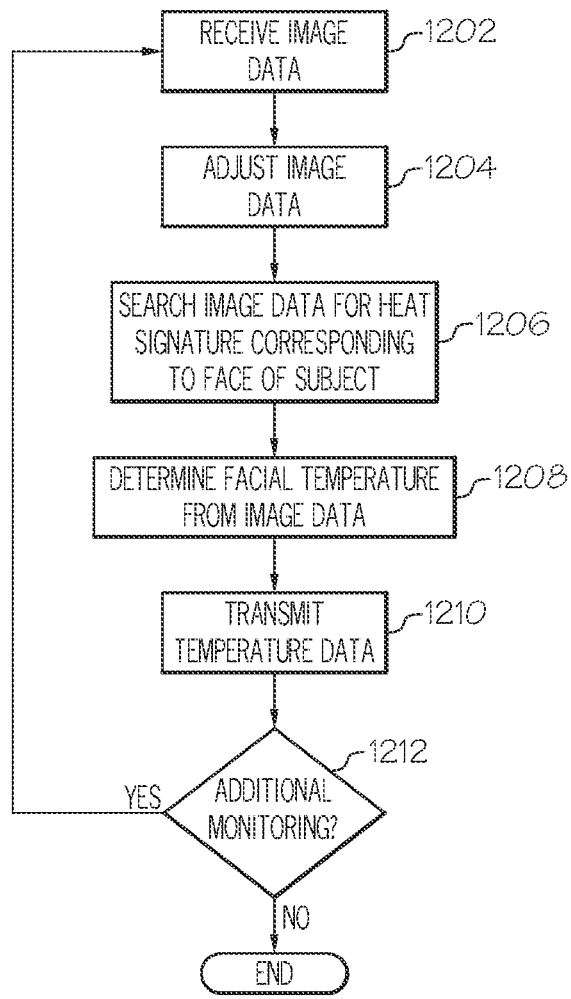
FIG. 12 depicts a flow diagram of an illustrative method of determining a subject temperature using a subject monitoring system according to one or more embodiments shown or described herein.

FIG. 12 depicts additional detail regarding a method of determining a facial temperature of the subject's face $F_S$. Referring to FIGS. 1, 2, and 12, the processing device 210 receives image data at block 1202. That is, the first imaging component 112 and/or the second imaging component 114 provide image data that is received by the processing device 210. At block 1204, the processing device adjusts the image data that is received such that the subject S can be adequately discerned for the purposes of determining facial temperature. For example, the image data may be adjusted by stitching or otherwise combining first image data from the first imaging component 112 and second image data from the second imaging component 114 to obtain a composite image that includes RGB image data relating to the shapes of objects in the field of view of the second imaging component 114 and thermal image data relating to an amount of thermal radiation given off by the subject S and/or other surrounding objects. In another example, the processing device 210 may adjust the sensitivity, color, and/or the like of the image data so as to produce images that depict the subject S, particularly the subject's face $F_S$, such that an accurate temperature reading can be obtained. Other means of adjusting the image data should generally be understood.

At block 1206, the processing device 210 searches the image data for a heat signature that corresponds to the face $F_S$ of the subject S and determines the facial temperature at block 1208. As described herein, such searching and determining processes with respect to blocks 1206 and 1208 steps may generally be completed as part of using a facial recognition algorithm and/or a shape recognition algorithm to determine the outline of the subject's face $F_S$ within the image data and associating a color of the pixels within the face with a particular temperature. At block 1110, the boundaries 134 of the patient support apparatus 130 are determined, as described herein.

At block 1210, the processing device 210 transmits temperature data corresponding to the determined temperature of the subject's face $F_S$. That is, data corresponding to the facial temperature may be transmitted to the user device 140 for display on the user device 140 to a user, transmitted to the server computing device 410 (FIG. 4) for storage, and/or the like.

As previously discussed herein, the monitoring device 110 may continuously monitor the subject for facial temperature by receiving a constant stream of image data (e.g., a video feed) from the first imaging component 112 and/or the second imaging component 114. Accordingly, the processing device 210 determines whether additional monitoring of the subject's face $F_S$ is necessary at block 1212. Such a determination may generally be based on one or more inputs received from a user, whether the subject S is in the patient support apparatus 130 (e.g., within the field of view of the first imaging component 112 and/or the second imaging component 114), and/or the like. If additional monitoring is necessary (e.g., to continuously monitor the subject's face $F_S$), the process returns to block 1202 to receive new image data and monitor the facial temperature. If no additional monitoring is necessary, the process may end.

Figure 13:
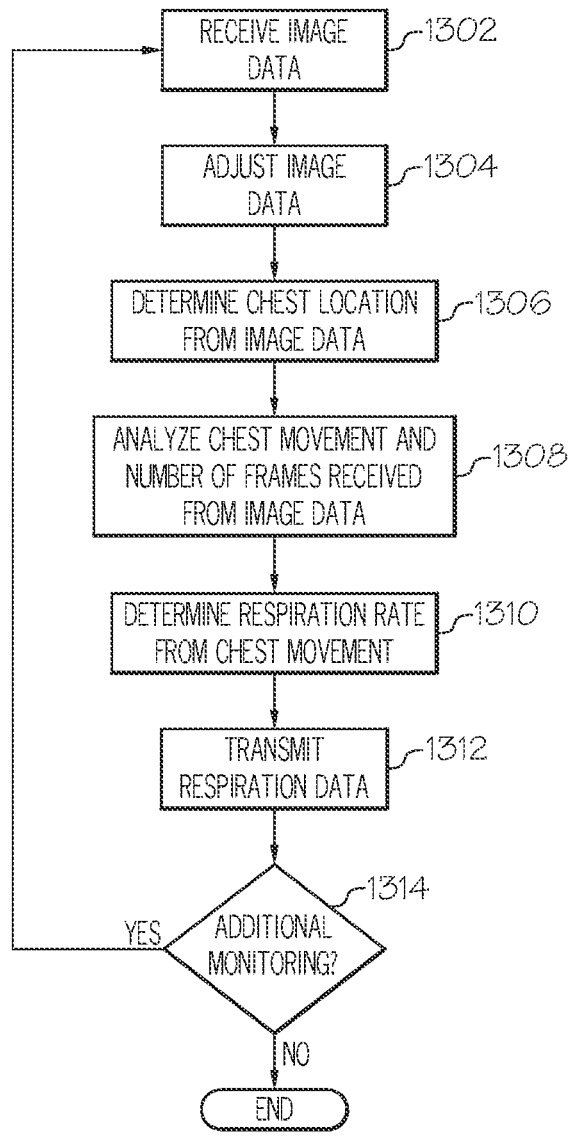
FIG. 13 depicts a flow diagram of an illustrative method of determining a subject respiration rate using a subject monitoring system according to one or more embodiments shown or described herein.

FIG. 13 depicts additional detail regarding a method of determining a respiration rate of the subject S. Referring to FIGS. 1, 2, and 13, the processing device 210 receives image data at block 1302. That is, the first imaging component 112 and/or the second imaging component 114 provide image data that is received by the processing device 210. With respect to FIG. 13, the image data generally includes a plurality of still images obtained in a particular period of time, a video stream, or the like. Still referring to FIGS. 1, 12, and 13, at block 1304, the processing device adjusts the image data that is received such that the subject S can be adequately discerned for the purposes of determining chest expansion and contraction. For example, the image data may be adjusted by stitching or otherwise combining first image data from the first imaging component 112 and second image data from the second imaging component 114 to obtain a composite image that includes RGB image data relating to the shapes of objects in the field of view of the second imaging component 114 and thermal image data from the first imaging component 112 relating to an amount of thermal radiation given off by the subject S and/or other surrounding objects. In another example, the processing device 210 may adjust the sensitivity, color, and/or the like of the image data so as to produce images that depict the subject S, particularly the subject's chest area, such that an accurate respiration rate determination can be made. Other means of adjusting the image data should generally be understood.

At block 1306, the processing device 210 determines the chest location from the image data. As described herein, an object recognition algorithm may be used to determine the chest of the subject from the image data. Accordingly, the plurality of images (e.g., the video stream) received within the image data may be analyzed, particularly in the area identified as the subject's chest, for chest movement (e.g., contraction and expansion) and the number of frames in which a full cycle of movement (e.g., one contraction and one expansion movement) occurs at block 1308. Once the number of frames that pass during a full cycle of movement is determined, the processing device 210 can determine the respiration rate of the subject S based on the frame rate of the imaging device (e.g., the first imaging component 112 and/or the second imaging component 114) at block 1310. For example, if a full cycle of movement occurs in thirty (30) frames and the framerate of the image data is thirty (30) frames per second, then a determination may be made at block 1310 that one (1) breath is taken every second. Accordingly, the respiration rate of the subject S would be calculated as twelve (12) breaths per minute.

At block 1312, the processing device 210 transmits respiration data corresponding to the determined respiration rate of the subject S. That is, data corresponding to the subject's respiration rate may be transmitted to the user device 140 for display on the user device 140 to a user as described herein, transmitted to the server computing device 410 (FIG. 4) for storage, and/or the like.

As previously discussed herein, the monitoring device 110 may continuously monitor the subject for respiration rate by receiving a constant stream of image data (e.g., a video feed) from the first imaging component 112 and/or the second imaging component 114 beyond what is necessary for an initial determination of the respiration rate. Accordingly, the processing device 210 determines whether additional monitoring of the subject S is necessary at block 1314. Such a determination may generally be based on one or more inputs received from a user, whether the subject S is in the patient support apparatus 130 (e.g., within the field of view of the first imaging component 112 and/or the second imaging component 114), and/or the like. If additional monitoring is necessary (e.g., to continuously monitor the subject's respiration rate), the process returns to block 1302 to receive new image data and monitor the respiration rate. If no additional monitoring is necessary, the process may end.

Figure 14:
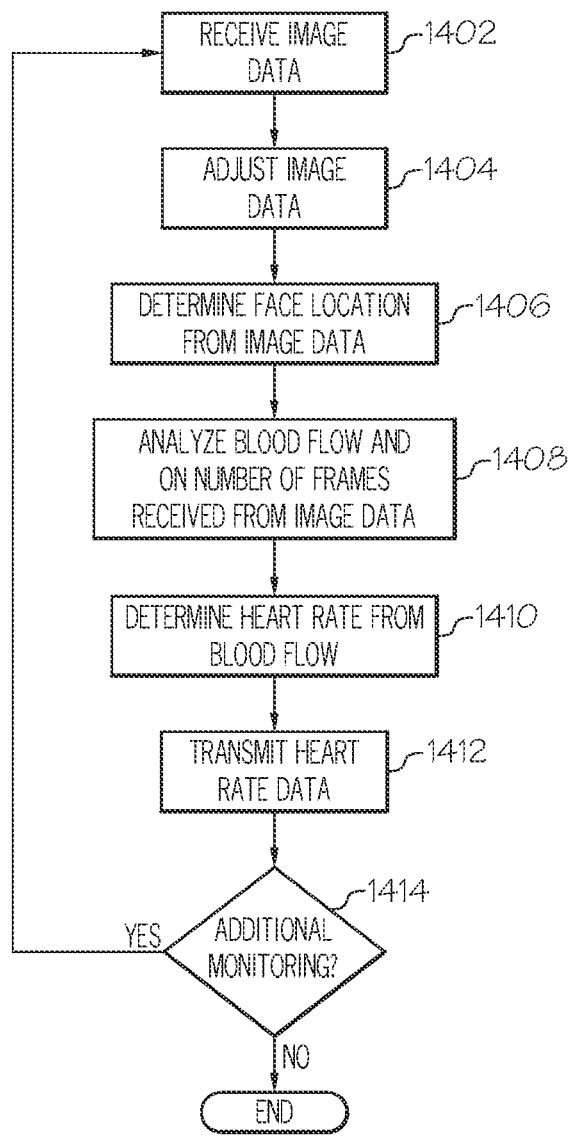
FIG. 14 depicts a flow diagram of an illustrative method of determining subject heart rate using a subject monitoring system according to one or more embodiments shown or described herein.

FIG. 14 depicts additional detail regarding a method of determining a heart rate of the subject S. Referring to FIGS. 1, 2, and 14, the processing device 210 receives image data at block 1402. That is, the first imaging component 112 and/or the second imaging component 114 provide image data that is received by the processing device 210. With respect to FIG. 14, the image data generally includes a plurality of still images obtained in a particular period of time, a video stream, or the like of the subject's face $F_S$. The image data generally corresponds to an amount of NIR light emitted from the one or more light emitting components 116 that is reflected by the subject's face $F_S$, which, in turn, can be used to determine an amount of NIR light that is absorbed by oxygenated blood in the capillaries of the subject's face $F_S$, as described herein. Still referring to FIGS. 1, 12, and 14, at block 1404, the processing device adjusts the image data that is received such that the subject's face $F_S$ can be adequately discerned for the purposes of determining an amount of NIR light that is being absorbed and reflected by the oxygenated blood in the capillaries of the subject's face $F_S$.

At block 1406, the processing device 210 determines the location of the subject's face $F_S$ from the image data. As described herein, a facial recognition algorithm may be used to determine the location of the subject's face $F_S$ from the image data. Accordingly, the plurality of images (e.g., the video stream) received within the image data may be analyzed, particularly in the area identified as the subject's face $F_S$, for blood flow and the number of frames in which a cardiac cycle occurs at block 1408 such that a coded hemodynamic imaging technique can be applied. More specifically, the processing device 210 determines the number of frames that have elapsed for the image to depict the subject's face $F_S$ as cycling from a minimum amount of NIR light absorption to a maximum amount of light absorption, as depicted in FIGS. 9A-9F, thereby indicating one cardiac cycle, as described herein. Once the number of frames that pass during a cardiac cycle is determined, the processing device 210 can determine the heart rate of the subject S based on the frame rate of the imaging device (e.g., the first imaging component 112 and/or the second imaging component 114) at block 1410. For example, if two (2) beats are observed in thirty (30) frames and the framerate of the image data is thirty (30) frames per second, then a determination may be made at block 1410 that the heart is beating twice every second. Accordingly, the respiration rate of the subject S would be calculated as one hundred and twenty (120) beats per minute.

At block 1412, the processing device 210 transmits heart rate data corresponding to the determined heart rate of the subject S. That is, data corresponding to the subject's heart rate may be transmitted to the user device 140 for display on the user device 140 to a user as described herein, transmitted to the server computing device 410 (FIG. 4) for storage, and/or the like.

As previously discussed herein, the monitoring device 110 may continuously monitor the subject for respiration rate by receiving a constant stream of image data (e.g., a video feed) from the first imaging component 112 and/or the second imaging component 114 beyond what is necessary for an initial determination of the heart rate. Accordingly, the processing device 210 determines whether additional monitoring of the subject S is necessary at block 1414. Such a determination may generally be based on one or more inputs received from a user, whether the subject S is in the patient support apparatus 130 (e.g., within the field of view of the first imaging component 112 and/or the second imaging component 114), and/or the like. If additional monitoring is necessary (e.g., to continuously monitor the subject's heart rate), the process returns to block 1402 to receive new image data and monitor the respiration rate. If no additional monitoring is necessary, the process may end.

It should now be understood that the systems and methods described herein accurately and concurrently determine the positioning, movement, facial temperature, heart rate, and respiration rate of a subject in a patient support apparatus using a monitoring device having an LWIR imaging device, an NIR and/or RGB imaging device, and one or more NIR light emitting devices. As a result, a subject in a patient support apparatus can be accurately tracked for movement and vital signs in a non-invasive, contactless manner. In addition, the monitoring device can be continuously operated such that information can continually be transmitted to a communicatively coupled user device that allows for remote monitoring of the subject.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A method of automatically monitoring a position and vital signs of a subject supported by a patient support apparatus, the method comprising:
  receiving, by a processing device of a monitoring device, long wave infrared (LWIR) image data from a first imaging component of the monitoring device and near infrared (NIR) image data from a second imaging component of the monitoring device;
  determining, by the processing device, one or more boundaries of the patient support apparatus from the NIR image data;
  constructing, by the processing device, one or more virtual boundaries that correspond to the one or more boundaries of the patient support apparatus;
  determining, by the processing device, a location of the subject with respect to the one or more virtual boundaries from at least one of the LWIR image data and the NIR image data;
  determining, by the processing device, a facial temperature and a heart rate of the subject from the LWIR image data;
  determining, by the processing device, a respiration rate of the subject from at least one of the LWIR image data and the NIR image data;
  transmitting the LWIR image data to a user device;
  transmitting the NIR image data to the user device;
  transmitting a composite of the LWIR image data and the NIR image data to the user device;
  display the LWIR image data as a first image at a first display area on a user device;
  display the NIR image data as a second image at a second display area on the user device; and
  display a composite of the LWIR image data and the NIR image data as a third image at a third display area on the user device simultaneously with the first image and the second image.

2. The method of claim 1, further comprising:
transmitting, by the processing device, at least one of the following to the user device: the LWIR image data, the NIR image data, data corresponding to the one or more virtual boundaries, data corresponding to the location of the subject, data corresponding to the facial temperature of the subject, data corresponding to the heart rate of the subject, and data corresponding to the respiration rate of the subject; and
directing, by the processing device, one or more light emitting components to emit NIR light towards the subject, wherein determining the heart rate of the subject comprises determining, from the NIR image data, an amount of the NIR light emitted by the one or more light emitting components that is absorbed by oxygenated blood present in capillaries of a face of the subject over a period of time, wherein the amount of NIR light that is absorbed cycles between a maximum amount absorbed and a minimum amount absorbed, and wherein a heartbeat corresponds to each cycle.

3. The method of claim 1, wherein determining the one or more boundaries of the patient support apparatus from the NIR image data comprises utilizing an object recognition algorithm to determine the patient support apparatus from the NIR image data based on a shape and a size of the patient support apparatus and determine one or more edges of the patient support apparatus.

4. The method of claim 1, wherein determining the location of the subject with respect to the one or more virtual boundaries comprises utilizing one or more of a facial recognition algorithm and an object recognition algorithm to determine a subject head position from at least one of the LWIR image data and the NIR image data, establishing a point that corresponds to the subject head position, and tracking movement of the point as the subject head position changes.

5. The method of claim 1, wherein determining the respiration rate of the subject comprises utilizing an object detection algorithm to identify a subject chest cavity from the at least one of the LWIR image data and the NIR image data, and monitoring a chest expansion and contraction movement over a period of time.

6. A system for monitoring a position and vital signs of a subject supported by a patient support apparatus, the system comprising:
a user device; and
a monitoring device comprising:
a first imaging component that obtains long wave infrared (LWIR) image data of the subject;
a second imaging component that obtains near infrared (NIR) image data of the subject and the patient support apparatus;
a processing device; and
a non-transitory, processor-readable storage medium comprising one or more programming instructions thereon that, when executed, cause the processing device to:
receive LWIR image data from the first imaging component and NIR image data from the second imaging component,
determine one or more boundaries of the patient support apparatus from the NIR image data,
construct one or more virtual boundaries that correspond to the one or more boundaries of the patient support apparatus,
determine a location of the subject with respect to the one or more virtual boundaries from at least one of the LWIR image data and the NIR image data,
determine a facial temperature of the subject from the LWIR image data,
determine a heart rate of the subject from the NIR image data,
determine a respiration rate of the subject from at least one of the LWIR image data and the NIR image data,
transmit the LWIR image data to the user device,
transmit the NIR image data to the user device, and
transmit a composite of the LWIR image data and the NIR image data to the user device,
wherein the user device is programmed to:
display the LWIR image data as a first image at a first display area on the user device;
display the NIR image data as a second image at a second display area on the user device; and
display a composite of the LWIR image data and the NIR image data as a third image at a third display area on the user device simultaneously with the first image and the second image.

7. The system of claim 6, further comprising network interface hardware that communicatively couples the monitoring device to a network, wherein the non-transitory, processor-readable storage medium further includes one or more programming instructions that, when executed, cause the processing device to transmit at least one of the following via the network interface hardware to the user device: the LWIR image data, the NIR image data, data corresponding to the one or more virtual boundaries, data corresponding to the location of the subject, data corresponding to the facial temperature of the subject, data corresponding to the heart rate of the subject, and data corresponding to the respiration rate of the subject.

8. The system of claim 6, further comprising one or more light emitting components that emit NIR light, wherein the non-transitory, processor-readable storage medium further includes one or more programming instructions that, when executed, cause the processing device to direct the one or more light emitting components to emit the NIR light towards the subject.

9. The system of claim 8, wherein the one or more programming instructions that, when executed, cause the processing device to determine the heart rate of the subject further cause the processing device to determine, from the NIR image data, an amount of the NIR light emitted by the one or more light emitting components that is absorbed by oxygenated blood present in capillaries of a face of the subject over a period of time, wherein the amount of NIR light that is absorbed cycles between a maximum amount absorbed and a minimum amount absorbed, and wherein a heartbeat corresponds to each cycle.

10. The system of claim 6, wherein:
the first imaging component comprises a first optical axis;
the second imaging component comprises a second optical axis;
the first imaging component is oriented such that the first optical axis forms a first angle relative to a surface of the patient support apparatus;
the second imaging component is oriented such that the second optical axis forms a second angle relative to the surface of the patient support apparatus; and
the first angle is different from the second angle.

* * * * *